(12) United States Patent
Stanton et al.

(10) Patent No.: US 7,570,732 B2
(45) Date of Patent: Aug. 4, 2009

(54) METHODS AND APPARATUS FOR OBTAINING LOW-DOSE IMAGING

(75) Inventors: Martin Stanton, Concord, MA (US); Alexander Stewart, Waltham, MA (US); Edward Bullard, London (GB)

(73) Assignee: Dexela Limited, London (GB)

( * ) Notice: Subject to any disclaimer, the term of this patent is extended or adjusted under 35 U.S.C. 154(b) by 0 days.

(21) Appl. No.: 11/603,876

(22) Filed: Nov. 22, 2006

(65) Prior Publication Data

US 2007/0242794 A1   Oct. 18, 2007

Related U.S. Application Data

(63) Continuation-in-part of application No. 11/595,664, filed on Nov. 9, 2006.

(60) Provisional application No. 60/735,140, filed on Nov. 9, 2005.

(51) Int. Cl.
G01N 23/04 (2006.01)
(52) U.S. Cl. .............................. 378/7; 378/8
(58) Field of Classification Search ............... 378/4–20, 378/901, 108, 207
See application file for complete search history.

(56) References Cited

U.S. PATENT DOCUMENTS 5,025,463 A * 6/1991 Saito et al. ................... 378/19
6,163,589 A 12/2000 Vartanian
6,744,848 B2 6/2004 Stanton et al.
2002/0097830 A1 7/2002 Raupach
2003/0095624 A1 5/2003 Eberhard et al.
2005/0113681 A1 5/2005 DeFreitas et al.
2005/0226375 A1 10/2005 Eberhard et al.
2005/0238133 A1 10/2005 Koppe et al.
2007/0076842 A1* 4/2007 Tkaczyk et al. ................ 378/5

FOREIGN PATENT DOCUMENTS

WO   WO 2006/039809 A1   4/2006

OTHER PUBLICATIONS

PCT/US2007/024244, International Search Report and Written Opinion, Aug. 11, 2008.
International Search Report for International applicaiton No. PCT/US2007/024244 mailed May 23, 2008.

* cited by examiner

Primary Examiner—Hoon Song
(74) Attorney, Agent, or Firm—Wolf, Greenfield & Sacks, P.C.

(57) ABSTRACT

In one aspect, A method of imaging an object of interest positioned in an exposure area is provided. The method comprises obtaining projection data of the object by providing radiation to the exposure area and detecting at least some of the radiation exiting the object to form the projection data, performing a first reconstruction of the projection data to form at least one bootstrap image, obtaining first data based on information provided by the at least one bootstrap image, and performing a second reconstruction of the projection data based, at least in part, on the first data to form at least one second image.

18 Claims, 17 Drawing Sheets

METHODS AND APPARATUS FOR OBTAINING LOW-DOSE IMAGING

RELATED APPLICATION

This application is a continuation-in-part (CIP) of U.S. application Ser. No. 11/595,664 (hereinafter the '664 application) entitled "METHODS AND APPARATUS FOR OBTAINING LOW-DOSE IMAGING," by Stewart, et al., filed Nov. 9, 2006, which in turn claims priority to U.S. Provisional Application Ser. No. 60/735,140, entitled "PLANAR IMAGING METHODS AND TECHNIQUES," filed on Nov. 9, 2005, both applications of which are herein incorporated by reference in their entirety.

FIELD OF THE INVENTION

The present invention relates to radiation imaging, and more particularly, to obtaining projection data of an object by exposing the object to radiation from a plurality of view angles.

BACKGROUND OF THE INVENTION

Imaging apparatus that utilize relatively high energy radiation such as x-ray and gamma rays are widely used to obtain images of subject matter more or less opaque to electromagnetic energy in the visual spectrum. For example, x-ray imaging technology has been employed in a wide range of applications from medical imaging to detection of unauthorized objects or materials in baggage, cargo or other containers. X-ray imaging typically includes passing radiation (i.e., x-rays) through an object to be imaged. X-rays from a source passing through the object are attenuated according to the various absorption characteristics of the material which the radiation encounters. By measuring the extent of attenuation of radiation that exits the object (e.g., by comparing the intensity of radiation entering and exiting the object), information related to the density distribution of the object may be obtained.

Computer tomography (CT) techniques typically involve capturing x-ray attenuation information from a plurality of angles about an object being imaged to reconstruct a three dimensional (3D) volume image of the object. For example, to obtain attenuation information about an object, a radiation source and a detector (or an array of detectors) responsive to the radiation may be arranged about the object. Each detector in the array, for example, may generate an electrical signal proportional to the intensity of radiation impinging on a surface of the detector. The source and detector may be rotated around the object to expose the object to radiation at a desired number of angular orientations.

At each orientation, referred to as a view angle, the detector signal generated by each detector in the array indicates the total absorption (i.e., attenuation) incurred by material substantially in a line between the radiation source and the detector. Therefore, the array of detection signals at each view angle records the projection of the object onto the detector array at the associated view angle. For example, using a 2D detector array, the resulting detector signals represent the 2D density projection of the object on the detector array at the corresponding view angle. The signals generated by the detectors form, at least in part, projection data (or view data) of the object.

Projection data obtained from multiple view angles about the object may be used to compute a density distribution of the object (i.e., to determine density values for locations within the object). The process of converting projection data (i.e., attenuation as a function of view angle) to density data (i.e., density as a function of location within the object) is referred to as reconstruction. That is, density values are reconstructed from information contained in the projection data. Typically, density values are expressed as image data, i.e., pixel or voxel values in two-dimensional (2D) and three-dimensional (3D) images, respectively.

Many techniques have been developed for reconstructing projection data into image data. For example, filtered back-projection is a widely used technique to form images from projection data obtained from single or multiple view angles. In general, reconstruction methods are based upon an assumed relationship between the intensity of radiation impinging on a detector and the integral of the density distribution of the object along the line from the radiation source to the detector. For example, the intensity-density relationship of radiation penetrating matter may be characterized as:

$$I = I_0 e^{-\mu(z)} \qquad (1),$$

where $I_0$ is the intensity of the radiation emitted from the radiation source before penetrating the material, I is the intensity of radiation having penetrated the material through a thickness z, and $\mu$ is a material specific linear absorption coefficient related to the density of the material. The term "intensity," with respect to radiation, refers to the amount of radiation present in or passing through a given volume per unit of time, and is thus a measure of radiation flux. The difference between I and $I_0$ is assumed to be the result of absorption by material substantially along a ray between the radiation source providing the radiation at intensity I and the detector detecting the radiation at intensity $I_0$. Thus, the relationship in Equation 1 can be used to compute the integral of the $\mu$ values over z along the ray between source and detector. This measurement approximates the total density of material situated along the ray between the source and detector.

In radiographic images (i.e., images reconstructed from projection data obtained at a single view angle), the total density approximation may be used as, or may be proportional to, the corresponding pixel value in the reconstructed image. Thus, the appropriate computation may be made along each ray from the radiation source to each detector location to form an image of the object at the single view angle. In CT images, projection data from multiple view angles are obtained. As a result, the various rays along which integral $\mu$ values are obtained will intersect at different locations within the object, thus providing additional information about discrete $\mu$ values at the intersection points. Accordingly, the projection data from multiple view angles may be used to differentiate individual $\mu_i$ values along the ray to provide information in an additional dimension. That is, rather than having a single integral $\mu$ value along each ray, the information in intersecting rays from the multiple view angles may be correlated to determine $\mu_i$ values at discrete locations along each ray to provide a tomographic reconstruction of the density distribution.

DETAILED DESCRIPTION

As discussed above, conventional approaches to reconstructing images from projection data often rely on relatively simple intensity-density relationships (e.g., the relationship described above in Equation 1). However, such relationships are oversimplifications of the physical processes occurring as radiation penetrates matter. For example, radiation scattering, beam hardening, diffraction characteristics, spectrum distribution effects, etc., complicate the intensity-density relationship. Simplified intensity-density models often assume that all of the radiation intensity detected at a particular detector or detector location is a result of monochromatic transmitted radiation along a ray between the detector and the radiation source. As such, many conventional reconstruction methods ignore one or more of the above identified effects, resulting in artifacts in the reconstructed images.

Applicant has appreciated that considering one or more factors not accounted for in the simplified intensity-density relationship may facilitate obtaining higher quality images. In particular, information about the one or more factors may be used to modify projection data and/or to perform more accurate reconstructions, resulting in images that may be more reflective of the actual density distribution of an object from which the projection data was obtained. There are a number of factors that may complicate the simplified relationship that may be considered, including, but not limited to, radiation scatter and beam hardening, as discussed in further detail below.

Conventional reconstructions based on the simplified intensity-density relationship typically assume that radiation is either transmitted or absorbed along a straight line path between the radiation source and the radiation detector. However, the interaction between penetrating radiation and matter is not such a simple process. Radiation attenuation occurs as a result of a number of different phenomenon, including the photoelectric effect, Compton scatter (incoherent scatter), Thompson or Rayleigh scattering (coherent scatter), pair production, etc. As a result, intensity recorded at a detector or detector array may have resulted from interactions according to various different phenomenon. Accordingly, reconstructions that use the simplified intensity-relationship therefore may incorrectly assign density values as a result of the assumption that recorded intensity at the detectors resulted solely from transmitted radiation, as discussed in further detail below.

Figure 1:
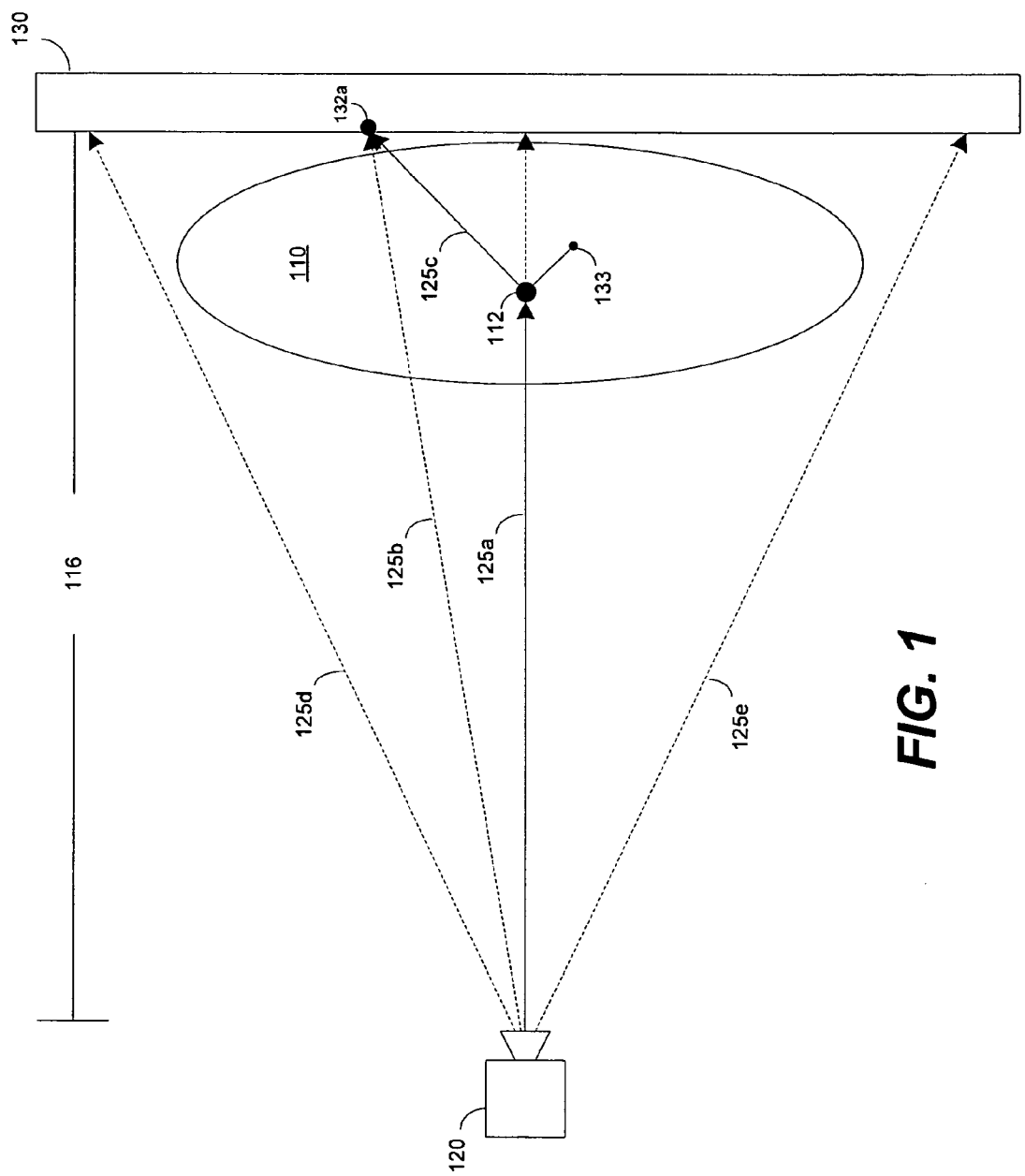
FIG. 1 is a diagram illustrating some of the effects of scattered radiation.

FIG. 1 is a schematic diagram illustrating the scatter phenomenon and the effects on image reconstruction using the simplified intensity density relationship. In FIG. 1, a radiation source 120 is arranged to provide radiation to an exposure area 116. For example, radiation source 120 may emit a beam of radiation from a source or focal point that radiates outward in the general shape of a cone. A 2D conic slice of a cone beam is illustrated in FIG. 1 (e.g., the conic slice bounded by rays 125$d$ and 125$e$). In particular, radiation source 120 may emit radiation propagating at various angles over the range bounded by rays 125$d$ and 125$e$. The cone-beam is directed to irradiate the exposure area, penetrating objects situated therein. Two exemplary rays 125$a$ and 125$b$, along which radiation may propagate, are shown to illustrate the scatter phenomenon.

Object 110 may be positioned in the exposure area such that radiation emitted from radiation source 120 penetrates the object. During exposure, a photon traveling along ray 125$a$ may interact with an atom 112 according to the Compton effect. As a result, an electron 133 is ejected from the shell of atom 112. In addition, a scattered photon is emitted along ray 125$c$. The scattered photon may then be transmitted through object 110 to impinge on detector 130 at detector location 132$a$. Because the simplified model assumes that radiation impinging on the detector was transmitted along a ray between the radiation source and the location on the detector at which the radiation was detected, the scattered photon will be treated as if it reached location 132$a$ along ray 125$b$. That is, the reconstruction algorithm will compute density values as if the scattered photon carried information about the density distribution along ray 125$b$, instead of along rays 125$a$ and 125$c$. Accordingly, failure to take Compton scatter into consideration may result in reconstruction errors.

Another factor that complicates the intensity-density relationship is beam hardening. Beam hardening relates to the phenomenon of preferential absorption of radiation energy. In general, radiation provided for the purpose of obtaining projection data of an object is polychromatic. That is, rather than the radiation having a single energy (monochromatic), radiation emitted from a radiation source will have an energy distribution comprising multiple energies. For example, radiation used in imaging exposures is often generated by directing an electron beam (e-beam) to strike a target surface. Common target materials include tungsten, molybdenum, rhodium, etc. The interaction of the e-beam with the target surface results in the emission of radiation comprised of multiple energies that are dependent on the target material type and the energy of the e-beam. That is, each target material will emit a characteristic energy distribution, or spectrum, in response to an impinging e-beam.

The e-beam is often generated in a vacuum tube, and has an energy proportional to a voltage potential between a cathode and anode (the target material) of the vacuum tube. As the energy in the e-beam increases, so does the energy of radiation emitted by the target. The energy of radiation is related to the electromagnetic wavelength of the radiation. Accordingly, the higher energy radiation refers to energy having shorter wavelengths and lower energy radiation refers to radiation having longer wavelengths. As discussed above, a target material will emit radiation having a characteristic spectrum as a result of an e-beam impinging on its surface.

Figure 2:
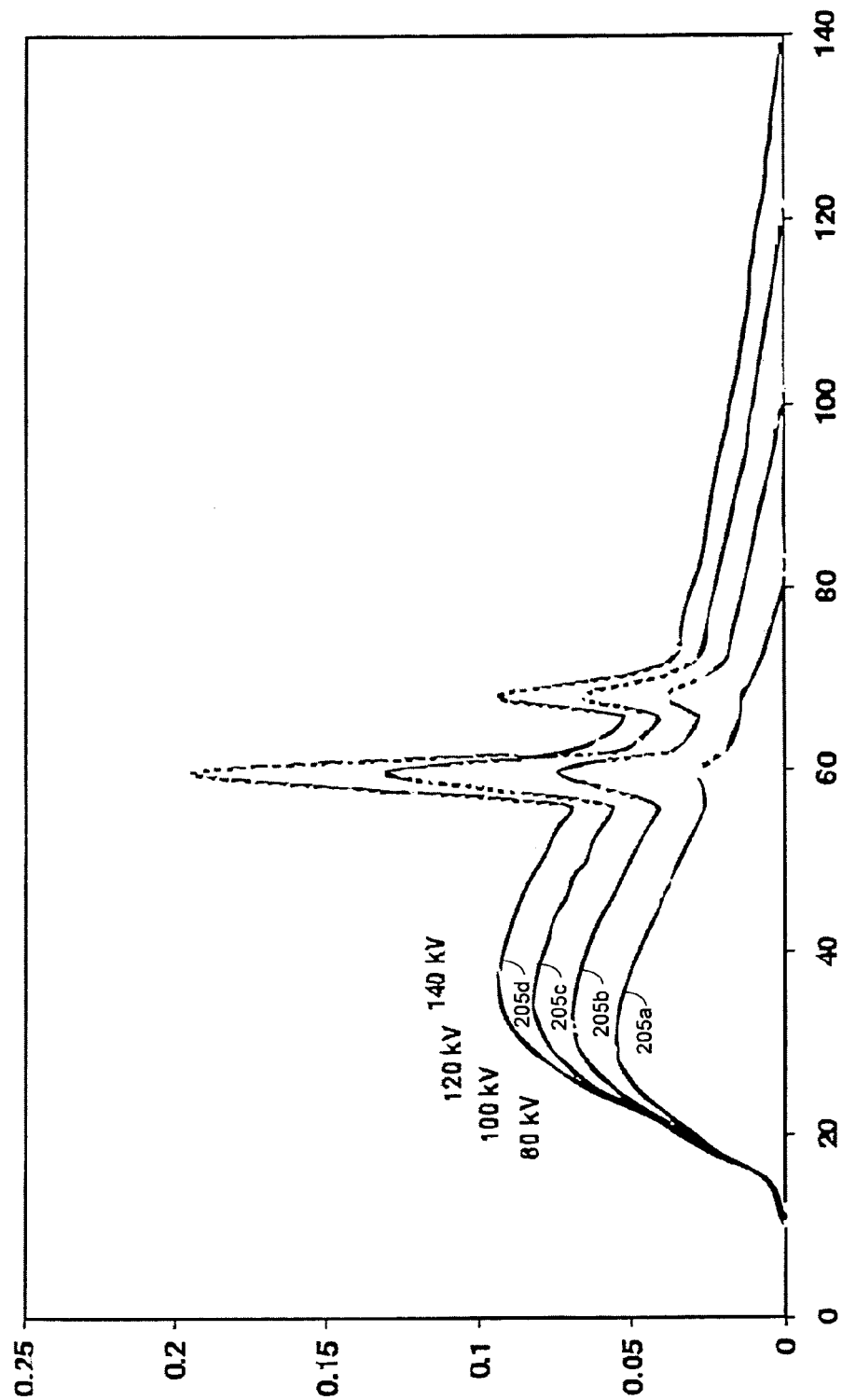
FIG. 2 is an illustration of a typical radiation spectrum obtained as a function of the voltage applied to an x-ray tube.

FIG. 2 illustrates the characteristic spectrum of tungsten at a number of energy levels of an e-beam. In particular, FIG. 2 includes a first spectrum 205a, a second spectrum 205b, a third spectrum 205c, and a fourth spectrum 205c resulting from bombarding a tungsten target with an e-beam generated at a voltage potential of 80 kilo-volts (kV), 100 kV, 120 kV and 140 kV, respectively. The energy spectrum includes two components, the Bremsstrahlung radiation, and the energy peaks characteristic of the target material. The Bremsstrahlung radiation is characterized by the generally continuous distribution of radiation that increases in intensity and shifts toward higher frequencies (shorter wavelengths) when the energy of the e-beam is increased. The energy peaks are the characteristic bands shown by the spikes at, for tungsten, 59 kilo-electron volts (keV) and 69 keV. As illustrated, increased e-beam energy increases the intensity of the peaks, but may not shift the peaks to higher frequencies.

Accordingly, radiation resulting from striking a target with an e-beam has an energy spectrum that depends, at least in part, on the energy in the impinging e-beam and the target material type. The energy spectrum of radiation is one factor that impacts the intensity detected at a detector array and complicates the simplified intensity-density relationship. Since lower energy radiation is absorbed more easily than higher energy radiation, the energy distribution of radiation (i.e., the energy spectrum) will change as the radiation penetrates matter.

In particular, the proportion of low energy radiation to high energy radiation will be different from the proximal side of the object (i.e., the side of the object closest to the radiation source) to the distal side of the object (i.e., the side of the object closest to the detectors). Specifically, the relative proportion of lower radiation will decrease with the thickness of the material being penetrated, leaving a larger proportion of higher energy radiation impinging on the detector array. This shift in proportion of higher energy radiation as a function of penetration depth is referred to as beam hardening.

Beam hardening impacts image reconstruction, in part, because radiation of different energies will react differently with the detector array. In particular, higher energy radiation, when absorbed, will generate larger detector signals than lower energy radiation. As a result, higher energy radiation will be interpreted as higher intensity radiation. In addition, higher energy radiation has a higher probability of passing through the detector without interacting with the detector lattice. Thus, when monochromatic radiation is assumed, the density values reconstructed from the recorded intensities may be incorrect due to the unaccounted for effects of polychromatic radiation.

Furthermore, the detection efficiency of a detector array may be a function of the energy of the photons in the radiation. For example, higher energy radiation may be detected less efficiently as the higher energy radiation may penetrate the sensing region of the detector without creating any signal. In addition, lower energy radiation may also be detected less efficiently as that radiation energy may fall below the threshold for detecting the radiation. Thus, most detectors have a radiation energy at which they are most efficient, and radiation energies both lower and higher that that will be detected less efficiently.

As discussed above, the detector response to radiation of different energies is typically a complex function of multiple factors. However, this relationship can generally be determined either experimentally or from the known characteristics of the detector. For example, to experimentally determine the response of the detector to various wavelengths, a series of measurements using monochromatic radiation at different energies can be used to characterize the response the detector will have to the spectrum of energies present in a polychromatic source of radiation. Alternatively, the physical properties of the detector can be used to calculate the response of the detector to radiation of different energies. For example, some detectors used in x-ray imaging employ a layer of selenium which is responsible for converting x-ray photons to electrons. In this case, the known properties of selenium and the thickness of the selenium can be used to calculate the response of the detector to the various energies in a polychromatic source.

As discussed above, projection data obtained from exposing an object to radiation comprises detector signals generated by the detectors in response to impinging radiation, the detector signals being indicative of the intensity of the radiation impinging on the respective detector. However, despite the apparent simplicity of the relationship between the detector signal and the density distribution of the exposed object suggested by Equation 1 (or other generally simplified intensity-density relationship models), the detector signals include information about a number of different factors simultaneously.

First, as indicated by the simplified model, the detector signals include information related to the amount of radiation that was transmitted through the object to impinge on the detectors. Second, as discussed above, the detector signals include information about the amount of radiation that was scattered by the object to impinge on the detectors. Third, the detector signals are impacted by the energy distribution of the impinging radiation.

However, in conventional imaging, the amount of intensity contribution to the detector signals attributable to each of the factors may not be capable of being separated from each other. That is, absent a priori information about the density distribution of the object, the relative contributions to the detector signals may not be differentiated, and are often thus simply ignored or assumed to have resulted from a single phenomenon. For example, the simplified model performs reconstruction by ignoring the second and third effects, e.g., by assuming the detector signals result only from monochromatic transmitted radiation.

In a departure from convention, various techniques may be used to obtain information that may be used to assist in differentiating the effects of one or more of the above described factors (e.g., radiation scatter, polychromatic energy spectrum, etc.) on projection data obtained from exposing an object to radiation. The information may be used to modify obtained projection data and/or to inform the reconstruction of the projection data to acquire an image that is more reflective of the actual density distribution within the object.

In some embodiments, one or more bootstrap images (i.e., initial reconstructions of obtained projection data) may be used to differentiate, to some extent, the intensity contribution attributable to the different factors that influence the detector signals. Information pertaining to the determined contributions may be used to inform a second reconstruction of the projection data to provide a more accurate reflection of the density distribution of the object being imaged. The one or more bootstrap images may be used, for example, to discriminate contributions attributable to transmitted radiation, scattered radiation and/or a polychromatic spectrum either alone or in any combination.

Information obtained from one or more bootstrap images may be used to modify projection data and/or inform subsequent reconstructions to improve image quality in other respects. In some embodiments, projection data obtained using an anti-scatter grid may be used to modify projection data obtained without using the anti-scatter grid to both compensate for and approximate the extent of scattered radiation. Images reconstructed from the modified projection data may better characterize the actual density distribution of the object because scatter effects have, to some extent, been accounted for.

In some embodiments, one or more density fiducials are positioned near an object being imaged during exposures, such that information corresponding to the density fiducials is present in projection data obtained from the object, and represented in one or more bootstrap images. The information in the one or more bootstrap images corresponding to the density fiducials may be used to modify the projection data and/or used to inform a subsequent reconstruction of the projection data. For example, the one or more density fiducials may be used to estimate scattered radiation, calibrate detector signals and/or assist in identifying a boundary of the object being imaged, such that subsequent reconstructions are more reflective of the actual density distribution within the object.

Following below are more detailed descriptions of various concepts related to, and embodiments of, methods and apparatus for practicing aspects of the present invention. It should be appreciated that various aspects of the invention described herein may be implemented in any of numerous ways. Examples of specific implementations are provided herein for illustrative purposes only. In addition, the various aspects of the invention addressed in the embodiments below may be used alone or in any combination, and are not limited to the combinations explicitly described herein.

Figure 3:
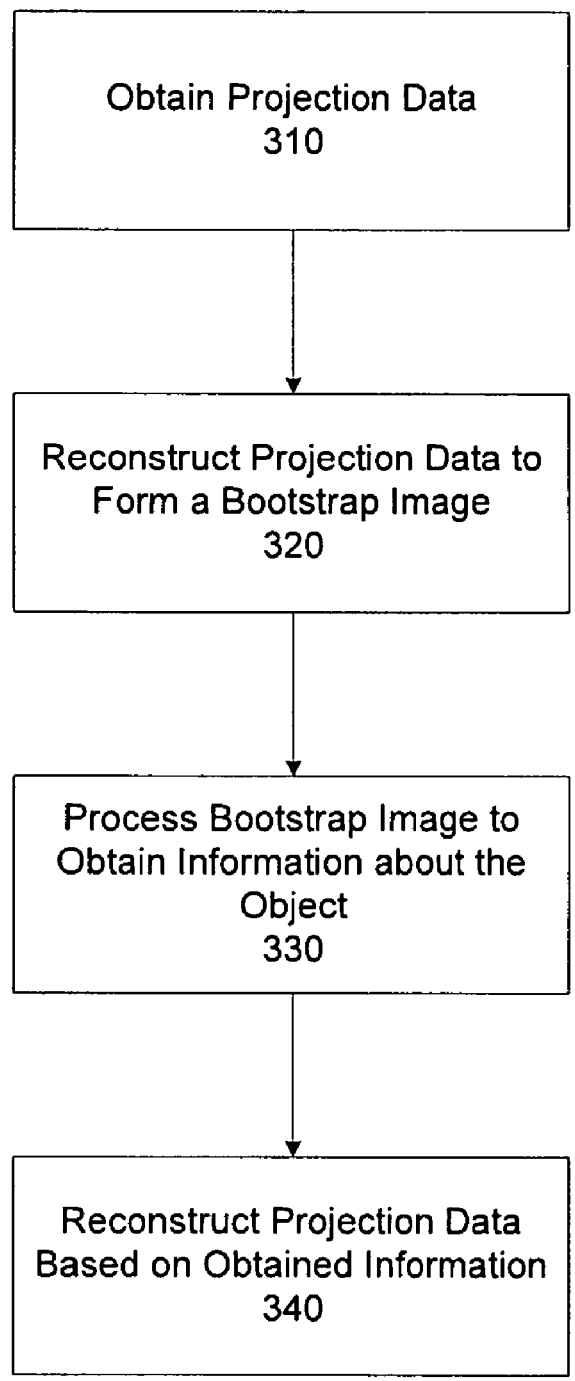
FIG. 3 is a flowchart illustrating a method for using information obtained from a bootstrap image to inform a subsequent image reconstruction, in accordance with some embodiments of the present invention.

FIG. 3 illustrates a method of improving image quality by using an initial image reconstruction (referred to as a bootstrap image) to characterize the density distribution of an object exposed to radiation to facilitate modeling one or more penetration effects, in accordance with some embodiments of the present invention. The term "bootstrap image" refers herein to an image of any dimensionality that is reconstructed to obtain information that may be used to modify projection data and/or to inform a subsequent reconstruction.

Unless otherwise indicated, a bootstrap image may be formed using any type of reconstruction method, and/or may be a full or only a partial reconstruction of acquired projection data. While a bootstrap image may be reconstructed according to relatively simple intensity-density relationships, the aspects of the invention are not so limited. In particular, a bootstrap image may be any collection of image data of any dimensionality (e.g., 2D, 3D, etc.) and may be reconstructed according to any desired reconstruction algorithm that transforms projection data into image data.

In act 310, projection data of an object is obtained from a selected view angle. For example, an object to be imaged may be exposed to radiation from a first view and the radiation exiting the object may be detected to collect attenuation information (i.e., projection data) at the selected view angle.

Act 310 may be repeated for any number of view angles to obtain projection data at a desired number and configuration views. For example, projection data may be obtained by exposing an object to radiation from one or more view angles distributed uniformly or non-uniformly about the object. U.S. Pat. No. 6,744,848 (hereinafter the '848 patent), entitled "METHOD AND SYSTEM FOR LOW-DOSE THREE-DIMENSIONAL IMAGING OF A SCENE," which is herein incorporated by reference in its entirety, describes various methods and apparatus for obtaining projection data of an object from a plurality of view angles in a relatively low dose environment. Any of the methods described in the '848 patent and/or disclosed in the incorporated parent application may be used to obtain projection data of the object. Other methods of obtaining projection data may be used as well, as the aspects of the invention are not limited in this respect.

The projection data may comprise the signal output of a two dimensional array of detectors arranged to detect radiation exiting the object. As discussed above, the signal output from each of the detectors may be used as an indication of the integral density of the object substantially along a line between the respective detector and the radiation source. For example, the smaller the detector signal, the more attenuation is assumed to have occurred along the propagation path of the radiation, thus indicating relatively dense material along the corresponding path. It should be appreciated that other methods of obtaining projection data may be used, as the aspects of the invention are not limited in this respect.

In act 320, the projection data obtained from the one or more view angles is then reconstructed to form image data from the projection data. That is, the projection data is transformed into values indicative of the density distribution of the object. The image reconstruction performed in act 320 may be performed according to a relatively simple intensity-density model to provide a bootstrap image. In particular, the detection signals forming the projection data may be assumed to have resulted from transmitted monochromatic radiation, and therefore reconstruction may be performed according to Equation 1, for example.

U.S. Pat. No. 5,872,828 (hereinafter the '828 patent), entitled "TOMOSYNTHESIS SYSTEM FOR BREAST IMAGING," which is herein incorporated by reference in its entirety, describes various methods for reconstructing a 3D image from projection data obtained from relatively few view angles (e.g., using substantially fewer view angles than in CT imaging). Any of the methods described in the '828 patent may be used to reconstruct a 3D image of the projection data obtained from the object. Any other suitable methods of reconstruction may be used, as the aspects of the invention are not limited in this respect.

As a result of performing simplified image reconstruction in act 320, bootstrap image may include errors associated with scatter and/or beam hardening effects that were not incorporated into the model used to reconstruct the bootstrap image. However, the bootstrap image may provide a useable approximation of the density distribution of the object. Information gleaned from the bootstrap image may then be used to determine, to some extent, contributions to the detector signals (i.e., recorded intensity of the radiation impinging on the detectors) attributable to one or more factors such as beam hardening, scatter, etc., and/or to otherwise obtain information that may be used to modify the projection data and/or inform a subsequent reconstruction.

In act 330, the bootstrap image is processed to glean information about the shape, structure and/or density distribution of the object to facilitate estimating what portions of the detectors signals resulted from any one or combination of penetration effects, and/or to determine other information that may be used to modify the obtained projection data and/or inform a second reconstruction of the projection data. For example, the density distribution in the bootstrap image may be used to approximate the exit spectrum to facilitate estimating the contribution to the detector signals from radiation of different energies to account for polychromatic effects, as discussed in further detail below in connection with FIG. 4.

Alternatively, or in addition, the shape of the object may be used to approximate the contribution to the detector signals from scattered radiation to account for scatter effects, as discussed in further detail below in connection with FIG. 5. It should be appreciated that other information may be extracted from the bootstrap image to facilitate differentiating the contributions of various effects on the obtained projection data (e.g., effects and contributions not modeled or accounted for using the simplified transmission model), as the aspects of the invention are not limited in this respect.

In addition, various methods of distinguishing contributions resulting from a respective phenomenon may be used alone or in combination with other methods adapted to differentiate one or more effects arising from the interaction between radiation and matter, as the aspects of the invention are not limited in this respect. Alternatively, or in combination with information relating to various penetration effects, other information may be obtained from the bootstrap image to modify the projection data and/or inform a second reconstruction. For example, the boundary of the image may be identified to constrain a reconstruction, as described in further detail below.

In act 340, the information gleaned from the bootstrap image is used to modify the projection data and/or used to constrain, refine or otherwise inform a second reconstruction of the projection data to form a refined image. The second reconstruction, therefore, may incorporate additional effects into the computation, thus modeling the intensity-density relationship more accurately and/or the reconstruction may be based on information about the object that facilitates more accurate assigning of density values. As a result, the refined image resulting from the second reconstruction may be more reflective of the actual density distribution of the object. It should be appreciated that the second reconstruction may be performed in any number of ways (e.g., according to any of the methods described in the '828 and/or '848 patents), as the aspects of the invention are limited for use to any particular method of reconstruction.

It should be appreciated that the process can be repeated, resulting in continued improvement of the reconstructed image. For example, the second reconstruction may form an additional bootstrap image from which information is gleaned to inform a further reconstruction. The process of reconstructing bootstrap images to obtain information that informs a subsequent reconstruction may be repeated any number of time (e.g., for a fixed number of times, or until the difference between successive images is below some desirable threshold).

As discussed above, act 310 may be performed at a plurality of view angles to obtain projection data of the object at a number of desired views. For example, act 310 may be performed in accordance with any of the acquisition techniques described in the '848 patent and/or the '664 application. In some embodiments, the object undergoing exposure is a breast or other radiation dose sensitive tissue, and one or both of the radiation intensity and/or radiation energy is varied as a function of the view angle (which may be distributed uniformly or non-uniformly about the object). In addition, acts 320 and 340 may be performed according to any of the reconstruction methods described in the '828, '848 patent and/or the parent application to obtain 3D images of the object.

It should be appreciated that the second reconstruction may be performed on projection data that has already been obtained from the object. As a result, image quality may be improved without requiring the object to undergo further radiation exposure, making it suitable for (though not limited to) dose limited imaging procedures such as mammography. However, employing information obtained from one or more bootstrap images to modify the projection data and/or to inform a second reconstruction, may be used in generally dose insensitive environments as well, as the aspects of the invention are not limited in this respect.

Figure 4:
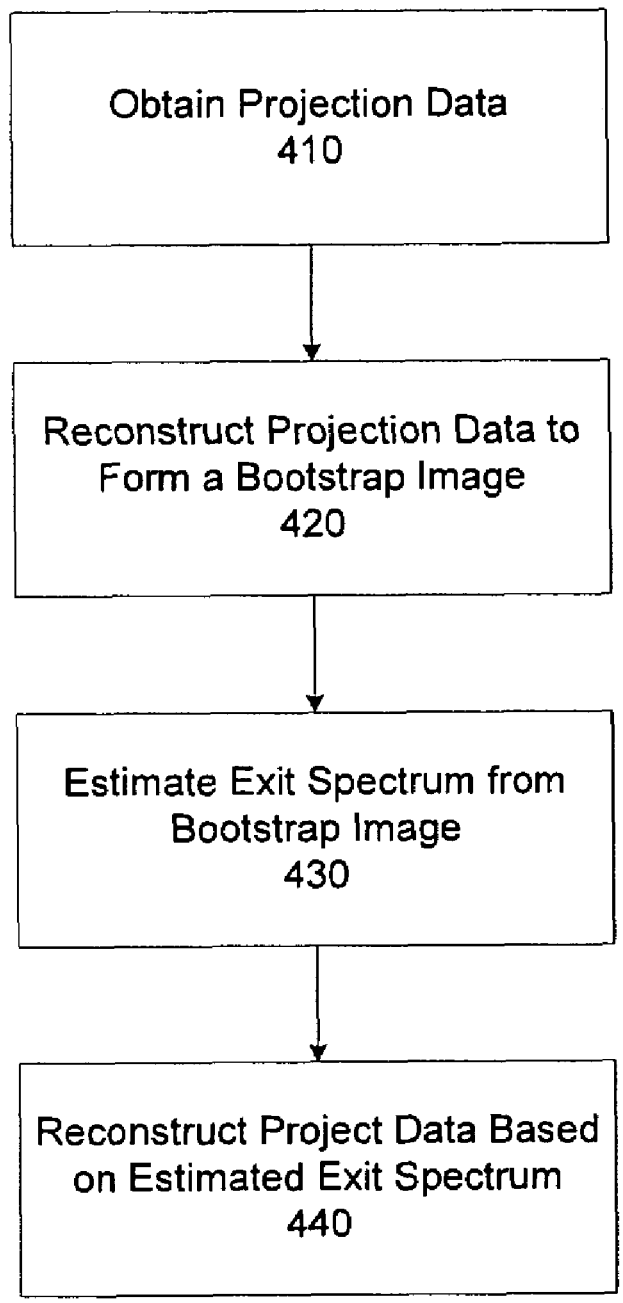
FIG. 4 is a flowchart illustrating a method for using information obtained from a bootstrap image to estimate an exit spectrum to inform a subsequent reconstruction, in accordance with some embodiments of the present invention.

FIG. 4 illustrates a method of obtaining information from an initial reconstruction to account for beam hardening effects, in accordance with some embodiments of the present invention. Acts 410 and 420 may be similar to the acts described in connection with FIG. 3. In particular, projection data may be obtained by exposing an object to radiation from a single or multiple view angles, and the projection data reconstructed to form a 2D or 3D bootstrap image of the density distribution, for example, by using a relatively simple transmission model for the intensity-density relationship. In some embodiments, the projection data is obtained from a plurality of view angles and reconstructed to form a 3D bootstrap image, according to any of the methods described in connection with the 848' patent, or otherwise. In particular, the projection data may be obtained in consideration of a relatively low dose budget suitable for imaging sensitive tissue and/or performing routine or frequent imaging procedures (e.g., breast imaging).

In act 430, an exit spectrum of the energy transmitted through the object is estimated from information in the bootstrap image to facilitate incorporating beam hardening effects into a subsequent reconstruction process. That is, the distribution of energy in the radiation exiting the object and impinging on the detectors is approximated based on the bootstrap image. The estimated exit spectrum facilitates performing a more accurate reconstruction that accounts for a polychromatic energy spectrum. In particular, the intensity-density relationship used to reconstruct a refined image (act 440) may account for the fact that 1) higher energy radiation results in proportionately larger detection signals 2) radiation at different energies may be detected with different efficiencies, and 3) radiation at different energies have unique characteristic attenuation functions.

As discussed above, higher energy radiation is more transmissive than lower energy radiation. As a result, more lower energy radiation is typically absorbed by the object than higher energy radiation. Therefore, the energy spectrum of the radiation penetrating the object, and more particularly, the proportion of lower energy radiation to higher energy radiation will vary as a function of penetration thickness. As the radiation penetrates more material, the more the energy spectrum will be skewed in the direction of higher energy radiation due to the preferential absorption of lower energy radiation. Thus, the energy spectrum of the radiation may be substantially different at the detectors (exit spectrum) than it is at the radiation source (emission spectrum).

As a general matter, detectors used in imaging procedures generate a signal proportional to the intensity of radiation detected at a radiation sensitive surface of the detector. However, the detectors may not respond uniformly to radiation at every energy. In particular, higher energy radiation tends to produce larger detection signals for the same intensity. Furthermore, radiation at different energies may be detected with different efficiencies. Thus, a photon of relatively high energy may produce a larger detector signal then a photon of relatively low energy. However, when nothing is known about the energy spectrum, this energy-dependent response is typically ignored. That is, radiation of a given intensity is assumed to produce the same detection signal regardless of the radiation energy. The result is that the presence of higher energy radiation may produce detector signals that are disproportionately large compared to the true intensity of impinging radiation.

To complicate matters further, the skew in the energy spectrum resulting from beam hardening results in a disproportionate (but generally unknown) amount of higher energy radiation in the exit spectrum. The result is that, when the detection signals are interpreted without any information about the energy spectrum, the recorded intensity of the radiation may be inaccurately low or inaccurately high, depending, at least in part, on the density distribution of the object. In particular, when using a detector that creates a greater signal when higher energy photons are detected, relatively high density material tends to be assigned lower densities values when polychromatic effects are ignored, resulting in reduced contrast images.

Since the simplified intensity-density model used to reconstruct the bootstrap image assumes monochromatic radiation, a particular intensity of radiation received at the detector may be assigned a particular meaning with respect to the density of the object along the respective ray during reconstruction. That is, the radiation along the respective ray is assumed to have been uniformly attenuated according to a single exponential attenuation function, rather than preferentially attenuated according to multiple exponential attenuation functions that decay at different rates depending on the radiation energy.

In particular, the characteristic attenuation function expressed in Equation 1 assumes energy independence. However, an attenuation function that more accurately expresses the physical process of radiation penetrating matter can be expressed as, $$I(\lambda) = I_0(\lambda) e^{-f(\lambda, \mu)z} \quad (2).$$

As shown, the rate of attenuation is a function not only of the thickness z and the material specific absorption coefficient $\mu$, but a function of the energy $\lambda$ of the radiation as well. However, if the energy spectrum is unknown, some specific value of $\lambda_0$ must be selected (e.g., an estimated average energy) when performing reconstruction (e.g., the exit spectrum is assumed to be monochromatic radiation at some energy $\lambda_0$). Accordingly, impinging radiation of energies different than $\lambda_0$ will be reconstructed according to an incorrect attenuation function. Thus, the monochromatic assumption may result in incorrect reconstruction of density values in conventionally reconstructed images.

By estimating the exit spectrum, the appropriate meaning may be assigned to radiation received at the detectors. In particular, the estimate of what energies contributed to the detected radiation may allow the detection signals to be properly interpreted, and further, may permit reconstruction of the projection data to be performed using the appropriate exponential attenuation function. For example, the exit spectrum indicates how much of the detected radiation intensity is attributable to different energy levels. Thus, the total detected radiation intensity may be divided into sub-totals corresponding to the intensity attributable to the different energies in the spectrum. The sub-totals may then be individually reconstructed to form corresponding density values for that energy, and the individual density values may be combined to form a single density based on a more accurate polychromatic model of the intensity-density relationship.

The exit spectrum may be computed based on an estimated emission spectrum and the density values forming the bootstrap image. In particular, the energy spectrum emitted from the radiation source (i.e., the emission spectrum) may be approximated based on knowledge of the radiation generation process and the properties of any filters used between the radiation source and the object being exposed to the radiation. The density distribution represented by the bootstrap image may then be used to model the interactions of the penetrating radiation to estimate the effects on the emission spectrum, i.e., to approximate the spectrum of the radiation exiting the object.

The emission spectrum may be approximated by taking into consideration properties and characteristics of the imaging apparatus. As shown in FIG. 2, the energy spectrum emitted from a target at a given e-beam energy is generally known. In some circumstances, a filter may be positioned between the radiation source and the object to be exposed to filter out certain energies. The passband of the filter (if present) in combination with the known characteristic spectrums of the target material and known e-beam energy may be used to compute an approximate emission spectrum. Any known or obtainable characteristics of the imaging apparatus may be used to estimate and/or assist in estimating the emission spectrum, as the aspects of the invention are not limited in this respect.

By using the density distribution represented by the bootstrap image, the penetration effects on the emission spectrum may be approximated. In particular, the bootstrap image may be used to determine both the thickness of the object along the propagation paths associated with the various view angles, and the density distribution along those paths. This information may then be employed to compute the attenuation of radiation at the various energies comprising the emission spectrum, for example, according to the relationship shown in Equation 2. That is, since approximate density values (related in a known way to the $\mu$ values of matter within the object) and the thickness of the object along any desired propagation path can be obtained from the bootstrap image, and the initial intensity of radiation at the various energies are known from the approximate emission spectrum, the attenuation of radiation at each of the various energies may be computed to arrive at an approximation of the exit spectrum.

In act 440, the approximate exit spectrum may be used to reconstruct the projection data using a model that incorporates polychromatic effects. In particular, the exit spectrum may be used to determine what proportion of the detected radiation intensity is attributable to the different energies in the exit spectrum so that the detection signals can be properly interpreted. For example, once the exit spectrum is known, detector signals can be scaled up or down to more accurately reflect the actual intensity of the radiation at each of the various energies in the exit spectrum to account for the fact that higher energy radiation may result in larger detectors signals. In addition, each differentiated intensity amount can be treated according to the appropriate attenuation function so that reconstruction is more reflective of the actual attenuation of the radiation at each of the energies in spectrum.

Accordingly, the second reconstruction may account for any number of polychromatic effects to improve the accuracy of the reconstruction and the quality of the resulting image.

In some embodiments, multiple exposures at different radiation energy may be obtained from the same view angle to estimate at least some beam hardening effects. As discussed above, matter tends to attenuate lower energy radiation more readily than higher energy radiation. By obtaining projection data from the same view angle using different radiation energy, the resulting projection data may be compared to estimate the amount of beam hardening that occurred. In particular, the projection data may be compared to characterize how the object is attenuating radiation at different energy. This information may then be used to inform the reconstruction of the projection data to account for at least some beam hardening effects. One of the exposures at the same view angle may be a low-dose exposure. The resulting projection data may be scaled before comparing the projection data with the one or more other exposures performed at the same view angle. This allows the multiple exposures to be performed without significantly increasing the total dose received by the object during the imaging procedure.

As discussed above, a bootstrap image may also be used to approximate the amount of scattered radiation to correct the projection data and/or to inform a subsequent reconstruction of the projection data obtained from exposing the object to radiation, to account for at least some scatter effects. In particular, the contribution of scattered radiation to detector signals produced from impinging radiation may be estimated to assist in identifying portions of the detector signals resulting from transmitted radiation, such that a subsequent reconstruction avoids incorrectly reconstructing information from scattered radiation as if the information was derived from transmitted radiation.

Figure 5:
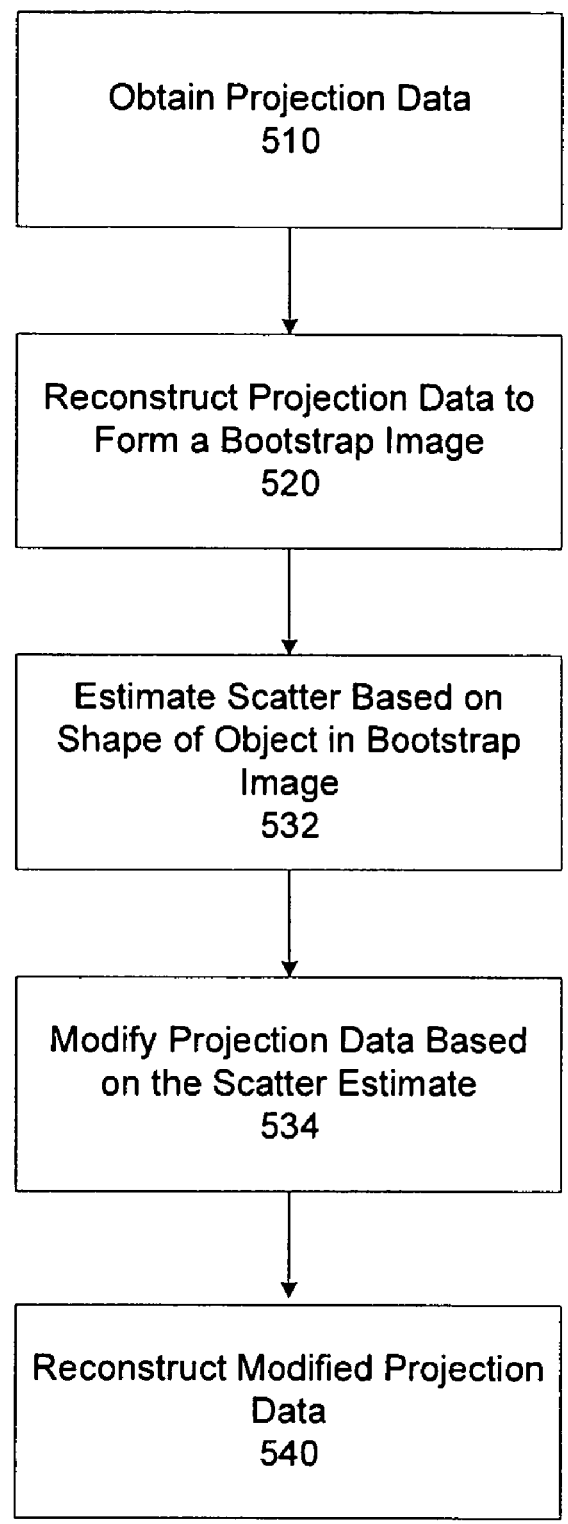
FIG. 5 is a flowchart illustrating of a method for using information obtained from a bootstrap image to estimate scattered radiation to inform a subsequent reconstruction, in accordance with some embodiments of the present invention.

FIG. 5 illustrates a method of obtaining information from an initial reconstruction to account for scatter effects, in accordance with some embodiments of the present invention. Acts 510 and 520 may be similar to the acts 310 and 320 described in connection with FIG. 3, and/or acts 410 and 420 in connection with FIG. 4. In particular, projection data may be obtained by exposing an object to radiation from a single or multiple view angles, and the projection data reconstructed to form a bootstrap image, for example, a 2D or 3D image from which characteristics of the object (e.g., density characteristics, shape information, size information, etc.) may be obtained.

In act 532, the information in the bootstrap image may be used to approximate detector signal contribution resulting from scattered radiation. As discussed above (e.g., in FIG. 1), radiation impinging on the detectors may have arrived at the detectors either via transmission (i.e., substantially along a ray between the radiation source and the detector) or via scattering (i.e., the radiation may have interacted with atomic subject matter according to the Compton effect). However, since the simple transmission models assume that all radiation impinging on the detectors is transmitted, reconstruction may not account for scattered radiation. A significant portion (e.g., up to approximately 50%) of detected radiation may be attributable scattered radiation. In view of assumptions made during reconstruction, portions of projection data resulting from scattered radiation serve as noise manifesting in image artifacts in the reconstructed image. Accordingly, an estimate of the scattered radiation may be used to correct the projection data such that resulting projection data is more reflective of purely transmitted radiation.

Figure 6A:
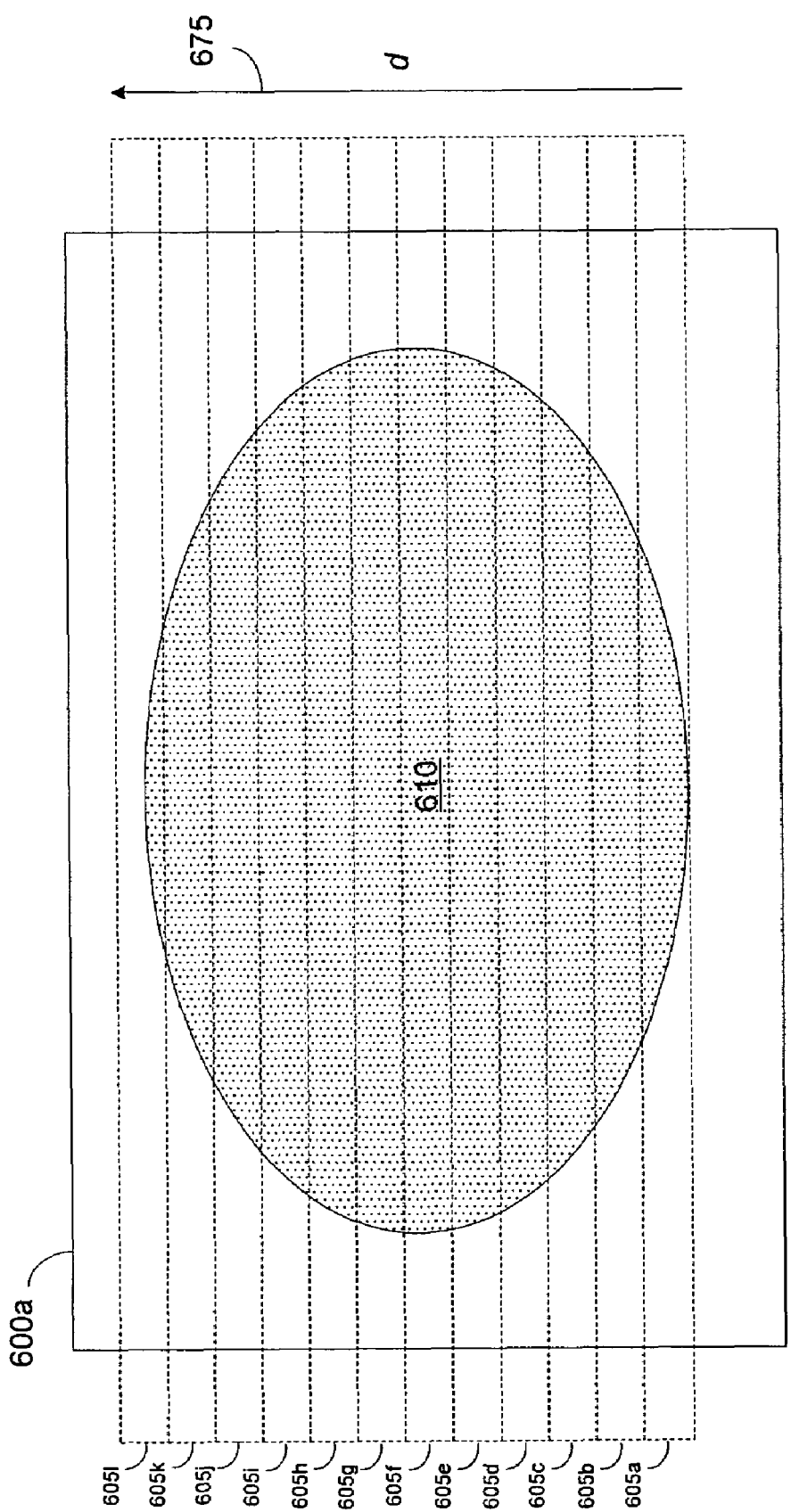
FIG. 6A is a diagram illustrating a method of estimating scattered radiation from a bootstrap image, in accordance with some embodiments of the present invention.
Figure 6B:
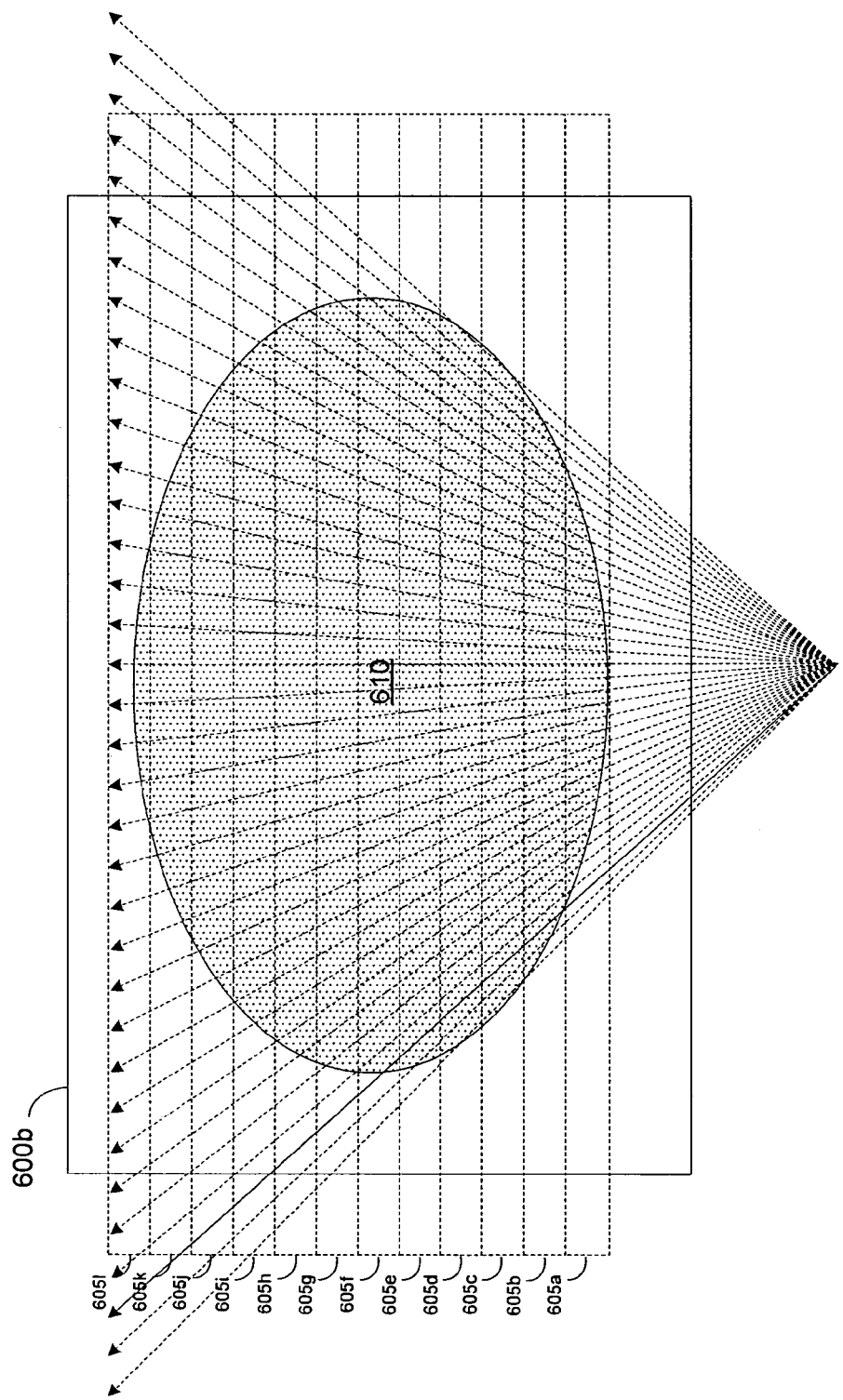
FIG. 6B is a diagram illustrating a method of estimating scattered radiation from a bootstrap image, in accordance with some embodiments of the present invention.

The amount of scattered radiation may be estimated by considering the shape of the object as represented in the bootstrap image. For example, FIGS. 6A and 6B illustrate embodiments for estimating scatter from a bootstrap image (e.g., embodiments that may be performed in act 532). In FIG. 6A, image 600a is a bootstrap image of an object 610. It should be appreciated that a real image of object 610 would include pixel values corresponding to the density distribution of and within the object. For simplicity of illustration, object 610 is shown as having a homogenous density distribution. In addition, images 600a and 600b are illustrated as 2D images, but may be, or be part of, 3D images as well (e.g., image 600a may be a 2D slice of a 3D image).

As discussed above, as radiation passes through an object, some proportion of radiation is scattered by the atomic structure of the object. Accordingly, each pixel (or voxel) in images 600a and 600b may be viewed as a scatter center from which radiation could potentially be scattered. The bootstrap image, therefore, may facilitate generating a model of the scatter by identifying where the density responsible for scatter is located. The probability that radiation will be scattered is a generally known or obtainable quantity. This probability increases as the radiation reaches increased penetration depths because there is more matter that could potentially scatter the radiation (i.e., the radiation has an increased likelihood of undergoing a Compton interaction with matter the more matter the radiation has penetrated).

This principle can be used to generate a model of the scatter (e.g., to generate an estimate of the contribution of scattered radiation on the projection data). In some embodiments, the bootstrap image of the object may be divided into a plurality of segments, each at successive depths of the object. For example, segments 605a-605l in FIG. 6A logically divide up image 600 at increased depths in a direction indicated by arrow 675, i.e., oriented generally away from radiation emitted by the radiation source. The contribution of scatter may be computed for each segment and then added together to estimate the total contribution of scattered radiation.

For example, the amount of the matter in segment 605a can be determined from the bootstrap image (e.g., the number of pixels or voxels in segment 605a may be counted to determine the number of scatter centers). The probability of radiation scattering at a depth d corresponding to segment 605a is generally known from the physics of the scatter phenomenon. Thus the number of scatter centers together with the probability of scattering at each scatter center at a given depth d may be used to approximate how much scatter radiation is generated in segment 605a. This computation may be repeated for each of the segments 605 and added together to approximate the amount of scatter resulting from radiation penetrating an object represented in the bootstrap image.

In some embodiments, the depths for which scatter is computed is based on the distance of the scatter centers (e.g., pixel or voxel locations) along rays extending from a focal point as illustrated in FIG. 6B. As discussed above, projection data may be obtained using a cone beam that fans out from the focal point of the radiation source. Rays representative of the propagation paths of radiation emitted during exposure may be logically superimposed on the bootstrap image and the penetration depth may be based on the distance along the respective rays from a location at which the ray first penetrated the object. By using rays indicative of the propagation paths of radiation used during exposures to obtain the projection data, a more accurate measure of penetration depth may be obtained. It should be appreciated that an estimate of radiation scatter based on the location of scatter centers identified in the bootstrap image may be obtained in other ways, as the aspects of the invention are not limited in this respect.

In act 534, the projection data may be modified in view of the estimated contributions of scattered radiation obtained from the bootstrap image. In particular, the effects of scattered radiation may be removed from the projection data such that the projection data is more representative of transmission effects only. That is, when the estimated detector signal contributions due to scattered radiation have been removed from the projection data, the projection data may more accurately reflect assumptions made during reconstruction (i.e., that the projection data arose from transmitted radiation). The modified projection data may then be reconstructed to form an image of the object that more correctly represents the density distribution of the object (act 540).

In some embodiments, multiple exposures at different radiation energy may be obtained from the same view angle to estimate scattered radiation. Radiation at different energy tends to be scattered by different amounts. By obtaining projection data from the same view angle using different radiation energy, the resulting projection data may be compared to estimate scattered radiation. The differences in the projection data obtained at different radiation energies will be partially attributable to the differences in how radiation at different energies is scattered. The estimate of the scattered radiation may then be used to modify the projection data to remove at least some of the contribution attributable to scattered radiation. The modified projection data may then be reconstructed to form one or more images. One of the exposures at the same view angle may be a low-dose exposure. The resulting projection data may be scaled before comparing the projection data with the one or more other exposures performed at the same view angle. This allows the multiple exposures to be performed without significantly increasing the total dose received by the object during the imaging procedure.

It should be appreciated that the techniques of incorporating polychromatic effects and scatter effects may be combined to further improve subsequent reconstructions. For example, information obtained from one or more bootstrap images to differentiate intensity contributions from transmitted radiation and scattered radiation, and to estimate and compensate for polychromatic effects may be used together to perform a reconstruction that more accurately reflects the actual density distribution of the object being imaged. In addition, the various methods of employing information from one or more bootstrap images to inform a subsequent reconstruction, can be used alone or in combination with other techniques for accounting for various penetration effects, as discussed in further detail below.

As discussed above, absent a priori knowledge, it may not be possible to differentiate contribution to detector signals from transmitted radiation and from scattered radiation. The foregoing describes, amongst other things, techniques for obtaining estimates of scattered radiation from one or more bootstrap images to remove at least some of the scatter effects in the resulting images. Anti-scatter grids yield another potential method for estimating scatter effects, in accordance with embodiments of the present invention. Conventionally, anti-scatter grids have been used to block scattered radiation from impinging on a detector array to ensure that substantially all of the impinging radiation at the detector array is transmitted radiation. However, conventional use of anti-scatter grids does not provide an estimate of scatter, but instead merely prevents scattered radiation from ever contributing to the projection data.

Figure 7:
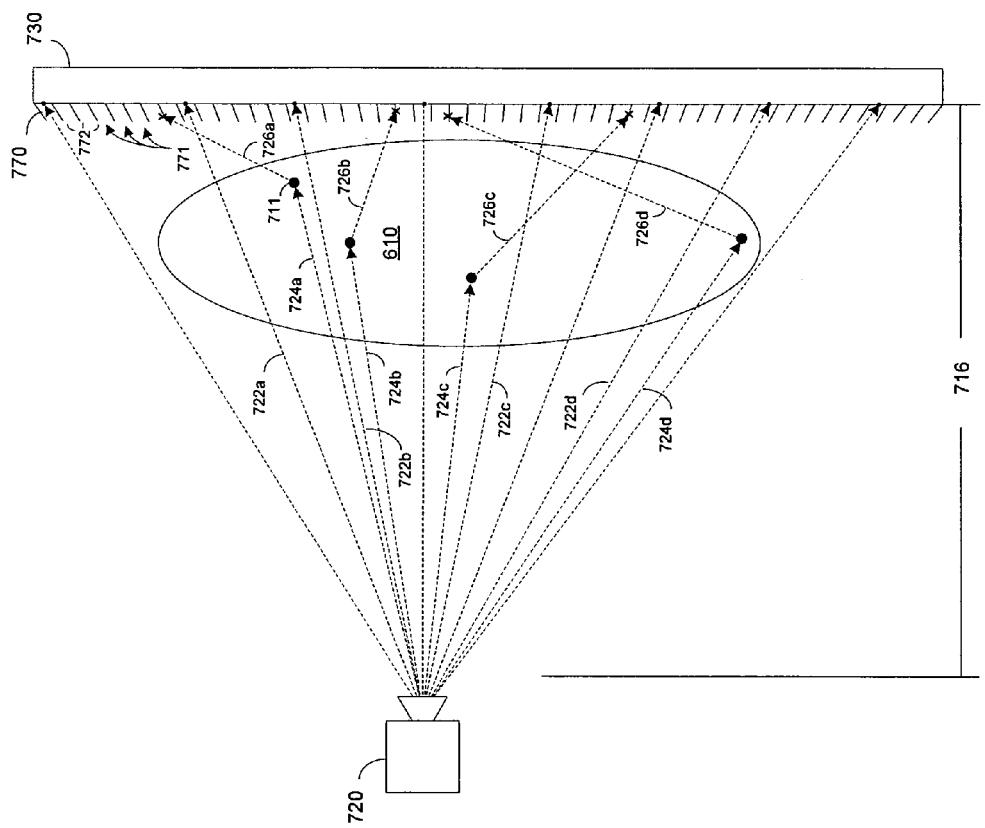
FIG. 7 is a diagram illustrating the use of an anti-scatter grid.

FIG. 7 illustrates concepts related to using an anti-scatter grid to prevent scattered radiation from impinging on a detector array. In FIG. 7, a radiation source 720 is arranged to provide radiation to an exposure area 716 where an object 710 may be positioned for exposure to the radiation. The radiation source 720 may provide, for example, a cone beam of radiation to the exposure area. A detector array 730 may be positioned beyond the exposure area to detect at least some of the radiation that penetrates and exits object 710 to obtain projection data of the object. An anti-scatter grid 770 may be positioned in front of the detector array to block radiation that is not propagating in a direction characteristic of transmitted radiation. In particular, anti-scatter grid 770 comprises a plurality of slots formed by a grid of dividers made from material of relatively high density (e.g., lead) adapted to absorb all or substantially all of the radiation impinging on the surface of the dividers (e.g., exemplary slots 771 and dividers 772). The dividers are angled in such a way that the propagation paths into the slots converge at the focal point of radiation source 720.

A number of exemplary rays, indicating possible radiation propagation paths, are shown to illustrate the function of the anti-scatter grid. The rays illustrate possible propagation paths in which radiation (e.g., photons) may travel from the radiation source through the exposure area. Rays 722 indicate exemplary propagation paths of transmitted radiation, i.e., radiation that does not interact with the atomic structure of object 710. The dividers 772 are angled such that radiation emitted from the focal point of radiation source 720 and passing unaffected through object 710 can impinge on the detector array via the slots 771.

Rays 724 illustrate potential propagation paths for scattered radiation, e.g., radiation that interacts with the atomic structure of object 710 according to the Compton effect. Due to the fact that scattered radiation is emitted from a source point (i.e., the atom from which it interacted) different than the focal point of the radiation source, the scattered radiation is unlikely to propagate in a direction that avoids impinging on one of the dividers. For example, radiation propagating along ray 724a undergoes a Compton interaction with an atom 711. As a result, radiation is emitted along ray 726a. Because the radiation has a different propagation path that does not converge with the focal point, the radiation along ray 726a will be absorbed by one of the dividers and prevented from impinging on the detector. Various other scattered propagation paths (e.g., paths 726b, 726c and 726c) are shown to illustrate how the anti-scatter grid prevents scattered radiation from impinging on the detector array and contributing to the detector signals forming projection data obtained from object 710.

Anti-scatter grids have been used conventionally to obtain projection data that is substantially free of the effects of scattered radiation. This projection data is then reconstructed to form an image of the structure of an exposed object. However, certain imaging geometries may be incapable of using an anti-scatter grid at multiple view angles. For example, some imaging equipment is designed to obtain projection data from a plurality of view angles by moving the radiation source about the object while leaving the detector or detector array stationary. As a result, an anti-scatter grid may be useable only at the single view angle where the slots are aligned with the focal point of the radiation source. In particular, an anti-scatter grid is typically designed to operate correctly only at a particular alignment with the radiation source. Accordingly, if the detector array and anti-scatter grid are not moved in correspondence, the anti-scatter grid may be thrown out of alignment such that even transmitted radiation will not reach the detectors. Accordingly, certain imaging equipment configurations may be unable to use anti-scatter grids at multiple view angles.

Applicant has appreciated that estimates of scatter obtained using information provided by an anti-scatter grid may be used both to modify projection data obtained at the view angle wherein the anti-scatter grid was used, and to modify projection data obtained from one or more other view angles where no anti-scatter grid was used and/or where no anti-scatter grid was available. Thus, imaging equipment, for example, wherein the radiation source and detector array do not move in correspondence may still benefit from scatter estimates obtained using an anti-scatter grid.

Figure 8:
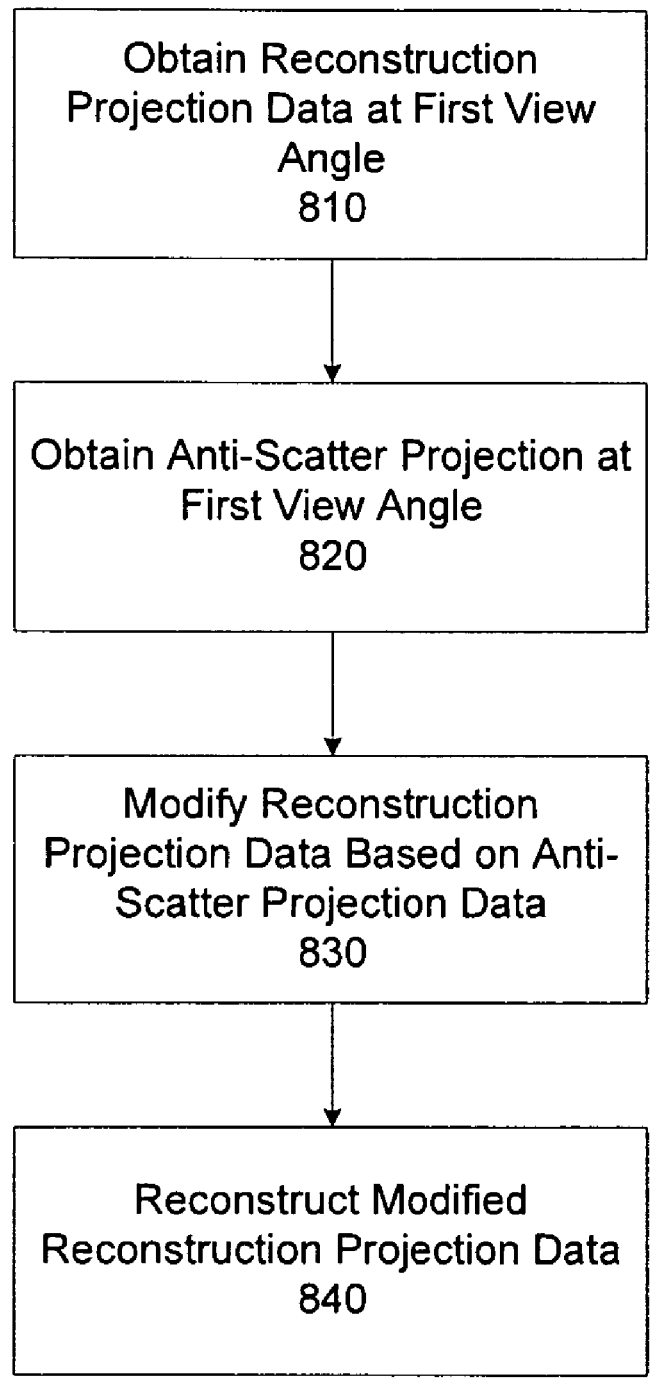
FIG. 8 is a flowchart illustrating a method of using an anti-scatter grid to estimate scattered radiation, in accordance with some embodiments of the present invention.

FIG. 8 illustrates a method of reducing the effects of scatter using an anti-scatter grid, in accordance with one embodiment of the present invention. In act 810, an object is exposed to radiation and first projection data is obtained. This first exposure may be performed without an anti-scatter grid, generally at the full dose that is appropriate for obtaining projection data of the object. For example, a dose budget may be set at an appropriate level for obtaining projection data from multiple view angles, and the dose for the first exposure may be an appropriate percentage of the total dose budget. Since the obtained projection data is intended for reconstruction to form one or more images (referred to as reconstruction projection data), the reconstruction projection data may be obtained at exposure levels sufficient to provide a desired resolution and contrast. As discussed above, the projection data obtained in this manner will include contributions from both transmitted and scattered radiation.

In act 820, a second exposure is performed at the same view angle using an anti-scatter grid to obtain anti-scatter projection data. The second exposure may be performed at a lower dose than the first exposure. The primary purpose of the anti-scatter projection data is to approximate the contribution of scattered radiation in detection signals produced in response to the first exposure and, more particularly, to compute the relative proportion of transmitted radiation to scattered radiation. Accordingly, the second exposure may be performed at a substantially lower dose because high resolution information (e.g., high contrast information) may not be required from the anti-scatter projection data. As a result, the second exposure may be performed without spending much of the intended total dose budget. For example, in breast imaging, the total subject dose received by the patient may be limited for safety purposes. Accordingly, by obtaining anti-scatter projection data at lower exposure levels, more of the dose budget is preserved for obtaining projection data that will ultimately be reconstructed to form images (e.g., diagnostic images of the breast).

In act 830, the reconstruction projection data obtained from the first exposure is modified based on the anti-scatter projection data obtained from the second exposure. In some embodiments, the difference between the anti-scatter projection data and the reconstruction projection data is computed. By subtracting the anti-scatter projection data from reconstruction projection data, the contribution of transmitted radiation is subtracted out, leaving substantially only the contribution of the scattered radiation. This difference (i.e., the estimate of the scatter effect) may then be subtracted from the reconstruction projection data to remove at least some of the contribution of the scattered radiation from the reconstruction projection data.

In embodiments where the first and second exposures are performed using different radiation doses, one or both of the reconstruction projection data and the anti-scatter projection data may need to be scaled to place the intensity values in the same range to permit appropriate comparison. For example, when the first exposure is performed at intensity and/or energy levels appropriate for obtaining relatively high contrast projection data (e.g., contrast suitable for producing diagnostic quality images), and the second exposure is performed using a reduced or substantially reduced dose, one or both of the projection data obtained may need to be scaled to ensure that any comparisons (e.g., differences) or modifications to the projection data is performed on data at the same scale.

In particular, if the anti-scatter projection data is obtained using emission intensities lower than those used to obtain the reconstruction projection data, the intensity of impinging radiation will naturally be lower as a consequence. As a result, the contributions of scattered radiation to the anti-scatter projection data will not be reflective of the contributions of scattered radiation to the reconstruction projection data, though the ratios may be similar. Accordingly, the anti-scatter projection data may be scaled up, or the reconstruction projection data may be scaled down to facilitate meaningful comparisons between the two sets of projection data. It should be appreciated that in embodiments where exposure levels are the same or similar for both exposures, scaling may be unnecessary.

In act 840, the modified projection data is reconstructed to form an image of the density distribution of the object which has been corrected for scatter effects. As a result, the image is reconstructed from projection data wherein contributions from scattered radiation have been reduced or eliminated. It should be appreciated that the exposures with and without the anti-scatter grid may be performed in either order, and the embodiment described above wherein the projection data without the anti-scatter grid is obtained first is merely exemplary, as the aspects of the invention may be used with projection data obtained in any order.

As discussed above, and described in the '848 patent, it may be advantageous to obtain projection data of an object from multiple view angles so that a 3D image of the object may be reconstructed. The '848 patent describes methods and apparatus for obtaining projection data from multiple view angles in a relatively low-dose environment such as imaging procedures involving human tissue and/or procedures that are performed regularly (e.g., low-dose environments suitable for breast imaging). The method of using projection data obtained with an anti-scatter grid to correct projection data obtained without an anti-scatter grid may be particularly suitable for such environments. Applicant has appreciated that estimates of radiation scatter obtained at one or more view angles may be used to approximate radiation scatter at other view angles at which actual exposures to collect scatter information are not performed, thus preserving more of the dose budget for exposures where relatively high resolution information may be needed.

Figure 9:
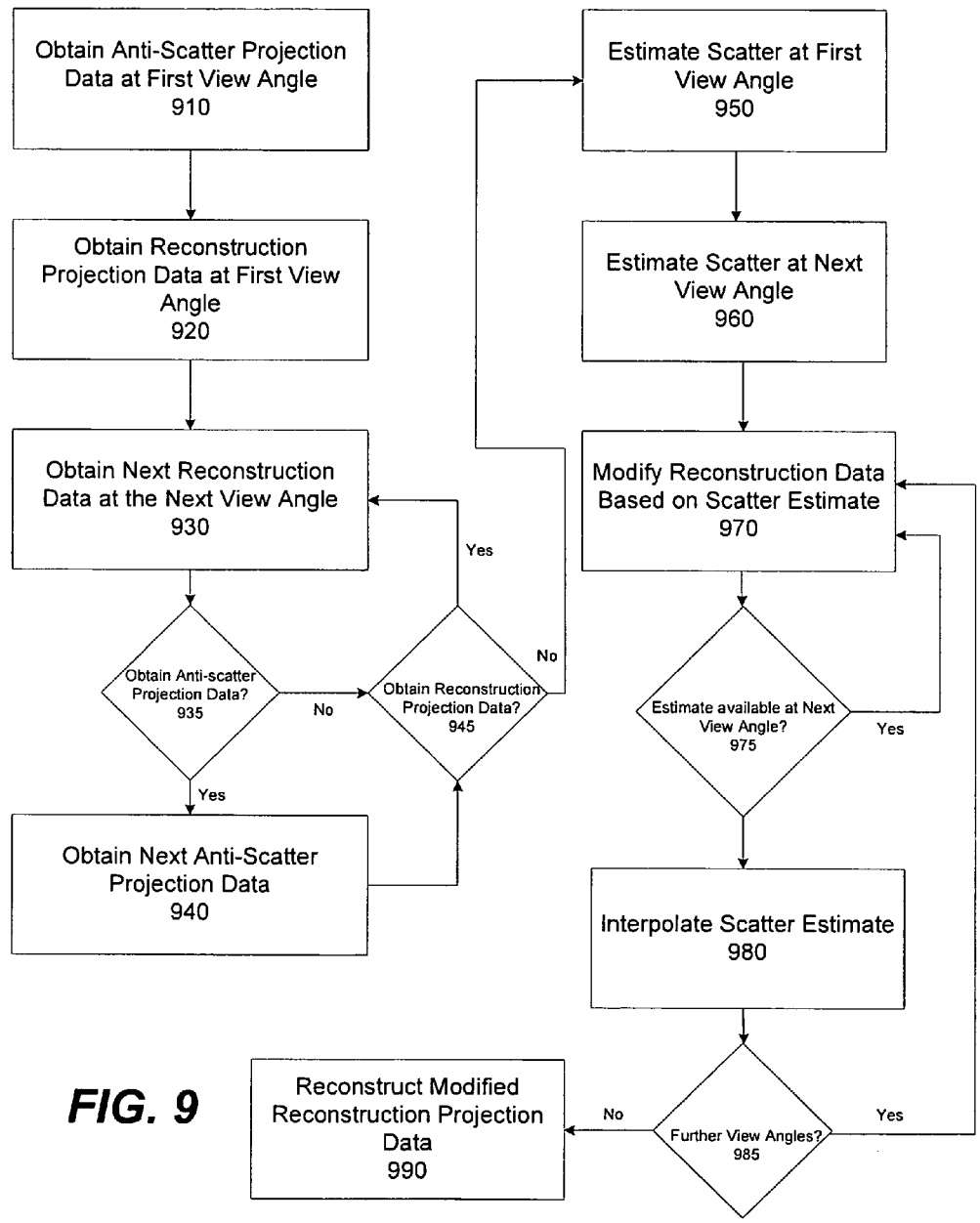
FIG. 9 is a flowchart illustrating a method of using an estimate of scattered radiation obtained using an anti-scatter grid at one view angle to modify projection data obtained at another view angle, in accordance with some embodiments of the present invention.

FIG. 9 illustrates one method of compensating for scatter effects in projection data obtained from a plurality of view angles, in accordance with one embodiment of the present invention. In act 910, anti-scatter projection data is obtained at a first view angle. In particular, an anti-scatter grid may be placed between the object and the detector array to absorb radiation scattered by the object. In some embodiments, the anti-scatter projection data is obtained using a lower dose than used to obtain subsequent first projection data to preserve the dose budget for exposures where resulting projection data is intended to be reconstructed to form image data. Since the anti-scatter projection data is obtained to correct for scatter effects in the higher dose projection data, it may be obtained under relatively low-does conditions with respect to exposures obtained for the purposes of image reconstruction. However, the reconstruction and anti-scatter projection data may be obtained at the same or similar exposure levels.

In act 920, first reconstruction projection data of an object is obtained at the first view angle without using an anti-scatter grid. In one embodiment, the first projection data is obtained at the full exposure allocated to each view angle in consideration of a particular dose budget (e.g., a dose budget suitable for safely performing mammography). Since the first reconstruction projection data will ultimately be reconstructed to form, at least in part, a 3D image, the projection data should be obtained at a relatively high resolution such that reconstructed images have the contrast necessary to properly distinguish the internal structure of the object (e.g., in breast imaging, the contrast should be high enough to accurately differentiate between healthy and anomalous breast tissue).

In act 930, next reconstruction projection data is obtained at a next view angle. Like the first reconstruction projection data, the next reconstruction projection data may be obtained at the full dose allocated for each view angle according to a given dose budget. In act 935, it is determined whether anti-scatter projection data should be obtained at the next view angle. As discussed above, anti-scatter projection data need not be obtained at each view angle that reconstruction projection data is obtained. In particular, anti-scatter projection data obtained from one or more view angles may be used to approximate scatter at other view angles, as discussed in further detail below. By estimating anti-scatter projection data, rather than obtaining the anti-scatter projection data via an additional exposure, preserves more of the dose budget for reconstruction projection data where high resolution/high contrast acquisition may be more important, and the dose budget more appropriately spent.

Depending on the determination made in act 935, either anti-scatter projection data is obtained at the next view angle (act 940), or a determination is made as to whether reconstruction projection data should be obtained at further view angles (act 945). If further reconstruction projection data is desired, the appropriate acts beginning at act 930 may be repeated. It should be appreciated that acts involved in performing exposures may be repeated any number of times to obtain reconstruction projection data and anti-scatter projection data at any desired view angles, respectively.

In some embodiments, the view angles at which reconstruction projection data is obtained form a range, and anti-scatter projection is obtained at least at the extremes and at the midpoint of the range, and otherwise interpolated, as described in further detail below. However, it should be appreciated that anti-scatter projection data may be obtained at any number and arrangement of view angles, as the aspects of the invention are not limited in this respect.

In some embodiments, anti-scatter projection data is obtained from a single view angle. The anti-scatter projection data may then be used to estimate the scatter at other view angle from which no anti-scatter projection data is obtained. For example, in imaging equipment that does not move the radiation source and radiation detector or detector array in correspondence when obtaining projection data from different view angles, an anti-scatter grid may be useful from only the single view angle for which it was adapted. Accordingly, anti-scatter projection data obtained from the view angle for which is was constructed may be obtained and subsequently employed to estimate the scatter at other view angles. It should be appreciated that anti-scatter projection data obtained from one view angle may be used to estimate scatter at another view angle even in the event that anti-scatter projection data could have been obtained from any of the view angles, as discussed in further detail below.

In act 950, an estimate of the scatter at the first view angle is obtained. For example, the scaled or unscaled difference between the first reconstruction projection data obtained at the first view angle and the anti-scatter projection data obtained at the first view angle may be used as an estimate of the scatter at the first view angle. However, an estimate of the scatter based on the projection data obtained with and without the anti-scatter grid may be computed in other ways, as the aspects of the invention are not limited in this respect.

In act 960, an estimate of the scatter at the next view angle where projection data was obtained (in the event that anti-scatter projection data was obtained for multiple view angles) both with and without an anti-scatter grid is computed. As discussed above, the estimate of the scatter may be performed by any suitable comparison between the reconstruction projection data and the anti-scatter projection data that provides a useful estimate of the scatter. Act 960 may be repeated for each view angle where both reconstruction projection data and anti-scatter projection data was obtained.

In act 970, the determined estimates of scatter from the one or more view angles are used to modify the reconstruction projection data to remove at least some of the effects of scattered radiation. For example, in the first instance, the estimate of the scatter at the first view angle may be subtracted from the first reconstruction projection data to remove at least some of the scatter effects. In act 975, it is determined whether an estimate of the scatter is available at the next view angle. In particular, since anti-scatter projection data may not have been obtained via an exposure at each of the plurality of view angles, some of the reconstruction projection data may not have a corresponding estimate of the scatter at the associated view angle.

If it is determined that an estimate of the scatter at a current view angle under consideration is present, then the reconstruction projection data is modified according to the corresponding estimate of the scatter (i.e., act 970 may be performed at the current view angle, and the next view angle may be assessed in act 975). If it is determined that no estimate of the scatter is available at the current view angle, then an estimate of the scatter at the current view angle may be determined from anti-scatter projection data and/or estimates of the scatter available at one or more other view angles (act 980).

In act 980, an estimate of the scatter at the current view angle is obtained from scatter information obtained at one or more other view angles where anti-scatter projection data was obtained via exposure. For example, the estimate of the scatter computed at the nearest lesser view angle and the nearest greater view angle may be used to estimate the scatter at the current view angle. In some embodiments, the estimate of the scatter at the current view angle is obtained by interpolating the estimate of the scatter from the nearest lesser and greater view angles. Alternatively, the estimate of the scatter may be obtained by using the anti-scatter projection data obtained at any of the view angles (e.g., the first view angle) for which an anti-scatter grid was used, as the aspects of the invention are not limited in this respect.

Once an estimate of the scatter is obtained, the estimate may be used to modify the reconstruction data at the current view angle to remove at least some of the effects of scattered radiation from the reconstruction projection data (e.g., act 970 may be performed on the current reconstruction projection data and the computed estimate of the scatter at the current view angle). It should be appreciated that anti-scatter projection data obtained via exposure may be used to form estimates of scatter at view angles where no anti-scatter projection data was obtained in other ways, as the aspects of the invention are not limited in this respect. The acts of correcting reconstruction view data based on estimates of the scatter (either obtained via exposure or computed from estimates obtained via exposure) may be repeated for each of the view angles at which reconstruction projection data was obtained.

In some embodiments, anti-scatter projection data is obtained from a single view angle and used to estimate scatter at the view angle from which it was obtained and each other view angle where reconstruction projection data was obtained. In some embodiments, a first exposure is performed from a reference view angle at a relatively high dose, and a number of subsequent exposures are obtained at slight rotations in view angle from the reference view angle and lower doses (e.g., as described in the '848 patent). Anti-scatter projection data may be performed at the reference view angle and used to estimate the scatter at the other view angles.

In act 990, the reconstruction projection data modified by the estimates of scatter may be reconstructed to form an image of the object, for example, a 3D image of the object. Because the projection data has had at least a portion of the scatter effects removed, the resulting image may more accurately reflect the actual density distribution of the object.

As discussed above, without any a priori information, it may be difficult to differentiate different contributions to the detector signals resulting from impinging radiation (e.g., contributions from transmitted radiation, scattered radiation, polychromatic radiation, etc.), which are often modeled as a single contribution (e.g., detector signals may be assumed to have resulted only from monochromatic transmitted radiation). Applicant has appreciated that using density fiducials during exposure of an object may provide information that may be used to facilitate differentiating contributions from one or more penetration effects, and/or otherwise providing information in a bootstrap image that may be employed to modify the projection data and/or inform a subsequent reconstruction.

The term "density fiducial" refers herein to material of generally known density positioned within an exposure area along with an object to be exposed such that at least some of some radiation passing through the exposure area impinges on the density fiducial. The term fiducial is used to indicate that typically the density and/or location of the fiducial is generally known a priori. A density fiducial positioned between a radiation source and the object is referred to as a proximal density fiducial (or located proximally) and a density fiducial positioned between the object and a detector array is referred to as a distal density fiducial (or located distally). A density fiducial may be of any desired density, shape or size, as the aspects of the invention are not limited in this respect.

In some embodiments, partially transmissive density fiducials (e.g., density fiducials that partially absorb and partially pass impinging radiation) are used to obtain information that can be used to modify projection data and/or facilitate more accurate reconstruction. In particular, by placing density fiducials of known density in known locations, a priori information is made available to the reconstruction. Partially transmissive density fiducials may be used, amongst other things, to both estimate scatter, to assist in calibrating detector signals, and to assist the reconstruction by providing a volume of known density, as discussed in further detail below.

Figure 10:
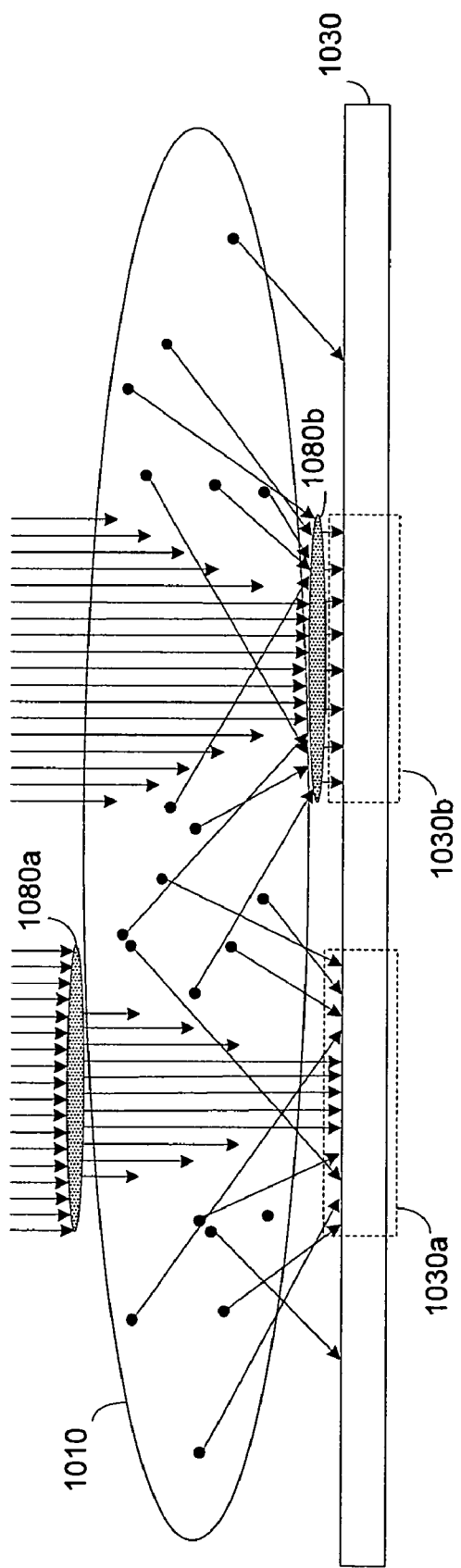
FIG. 10 is a diagram of using a proximal density fiducial and a distal density fiducial to estimate scattered radiation, in accordance with some embodiments of the present invention.

FIG. 10 illustrates concepts related to using partially transmissive density fiducials to obtain an estimate of scattered radiation, in accordance with some embodiments of the present invention. In FIG. 10, a first partially transmissive density fiducial 1080*a* is positioned proximally with respect to the object. That is, proximal fiducial 1080*a* is positioned between a radiation source (not shown) and the object 1010 being imaged. For simplicity of illustration, the radiation is illustrated as propagating along a plurality of parallel rays. However, it should be appreciated that non-parallel rays (e.g., the propagation paths of radiation emitted in a cone-beam) may be used as well, as the aspects of the invention are not limited in this respect. In particular, the concepts described in connection with FIG. 10 may apply to radiation fields of any shape and/or configuration. A second partially transmissive density fiducial 1080*b* may be positioned distally, such that at least some radiation penetrating through object 1010 interacts with density fiducial 1080*b*.

In the embodiment illustrated in FIG. 10, the density of the proximal and distal fiducials are chosen such that approximately 50% of radiation impinging on the fiducial will be transmitted and 50% will be absorbed. However, the density selected is merely exemplary and was chosen to best illustrate concepts related to using generally matched density fiducials to estimate scatter. Since density fiducial 1080*a* is placed proximally, the intensity reduction resulting from the fiducial is applied only to primary radiation (i.e., non-scattered radiation) because no substantial subject matter interacts with the radiation to cause scattering prior to impinging on density fiducial 1080*a*. To illustrate the principle, object 1010 is shown as absorbing about 50% of the radiation through the thickness underneath density fiducial 1080*a*. Accordingly, approximately 25% of the radiation impinging on proximal density fiducial 1080*a* is transmitted through the object to impinge on the detectors in the shadow of the fiducial.

Since density fiducial 1080*b* is placed distally, the intensity reduction resulting from the fiducial will be applied to all of the radiation impinging on the fiducial; both transmitted and scattered. As a result, the intensity reduction from the perspective of the detectors in the shadow of density fiducial 1080*b* will be more significant than the intensity reduction from the perspective of the detectors in the shadow of density fiducial 1080*a*. Accordingly, the difference between the intensity reduction from the respective density fiducials may be used to estimate the scatter.

For example, there is substantially the same amount of radiation absorbing subject matter between the radiation source and the detectors in the shadow of the respective density fiducials (i.e., the detectors in region 1030*a* and region 1030*b*, respectively). In particular, there are the density fiducials themselves (which may be identical or substantially identical is shape, size and/or density to each other) and substantially the same thickness of object 1010. In addition, substantially the same amount of scatter radiation will converge in the area directly above regions 1030*a* and 1030*b*. However, the detectors in region 1030*a* will record a greater intensity than the detectors in region 1030*b* due to the positioning of the density fiducials.

In particular, substantially all of the scattered radiation present in the object immediately above region 1030*a* will directly impinge on the detectors, while a substantially equal amount of scatter radiation present in the object immediately above region 1030*b* will be attenuated by density fiducial 1080*b*. Thus, detectors in region 1030*b* will record less intensity in an amount related to the absorption ratio of the density fiducials. As discussed above, this difference is related to amount of scattered radiation as illustrated in FIG. 10, and may be used to provide a scatter estimate that may be employed to modify the projection data to account for at least some scatter effects.

It should be appreciated that FIG. 10 is schematic and not drawn to scale. The relative size of the density fiducials with respect to the object was chosen to illustrate the concept of using proximally and distally positioned density fiducials to estimate scatter, and may not be indicative of actual relative sizes. In addition, the absorption characteristics of the density fiducials was selected to highlight the differential in intensity reduction. However, density fiducials of any density may be used, as discussed in further detail below.

Figure 11:
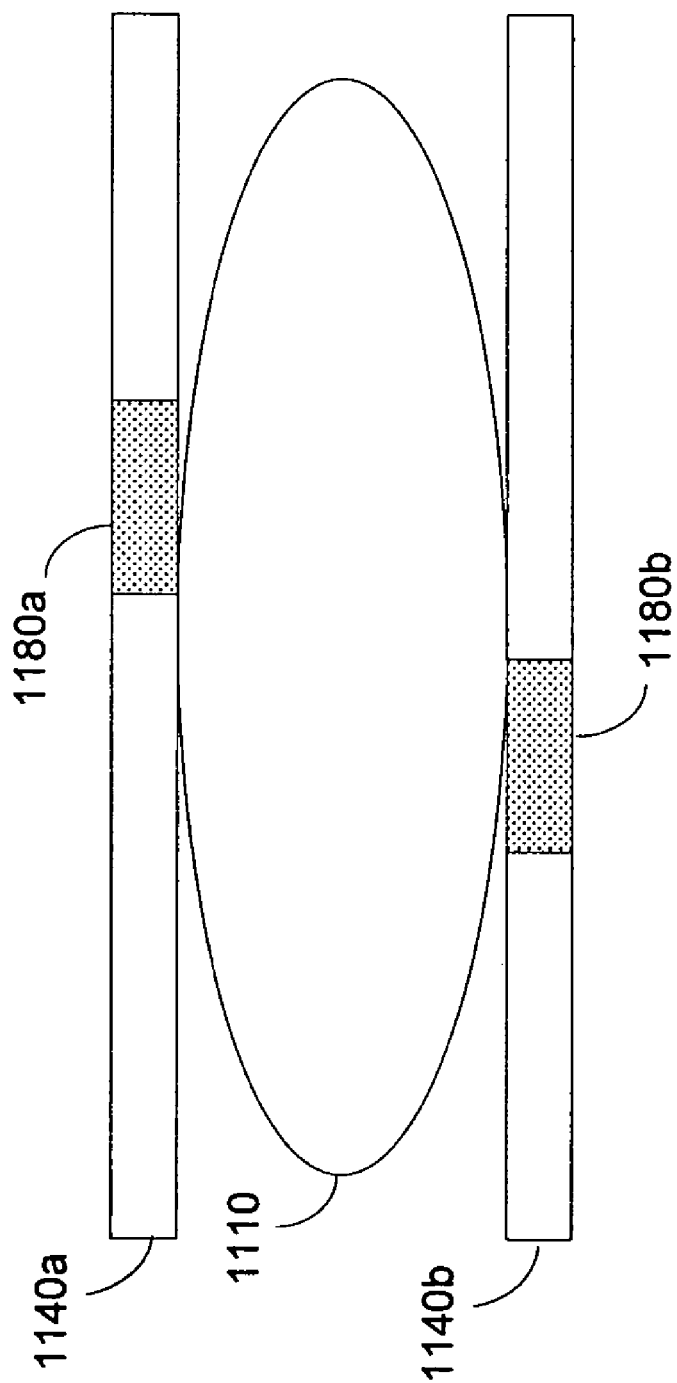
FIG. 11 is a diagram illustrating the incorporation of density fiducials in compression paddles used to position and compress a breast during a breast imaging procedure, in accordance with some embodiments of the present invention.

In some embodiments, the object being imaged is a human female breast and the density fiducials are a part of or affixed to the compression mechanism that positions and compresses the breast in preparation for imaging. For example, FIG. 11 illustrates a schematic diagram of a breast 1110. The breast is held in place and compressed by compression paddles 1130a and 1130b. Density fiducials 1180a and 1180b are implemented as portions of the compression paddles. In other embodiments, the density fiducials are affixed to the compression paddles so that they are removable, allowing density fiducials of any desired density to be positioned within an exposure area and employed to estimate scatter and/or calibrate detector signals. In still other embodiments, the density fiducials are affixed to the object itself. In still other embodiments, distal density fiducials are affixed to a portion of the detector array. It should be appreciated that density fiducials may be positioned and/or affixed proximally and distally in any manner, as the aspects of the invention are not limited in this respect.

Figure 12:
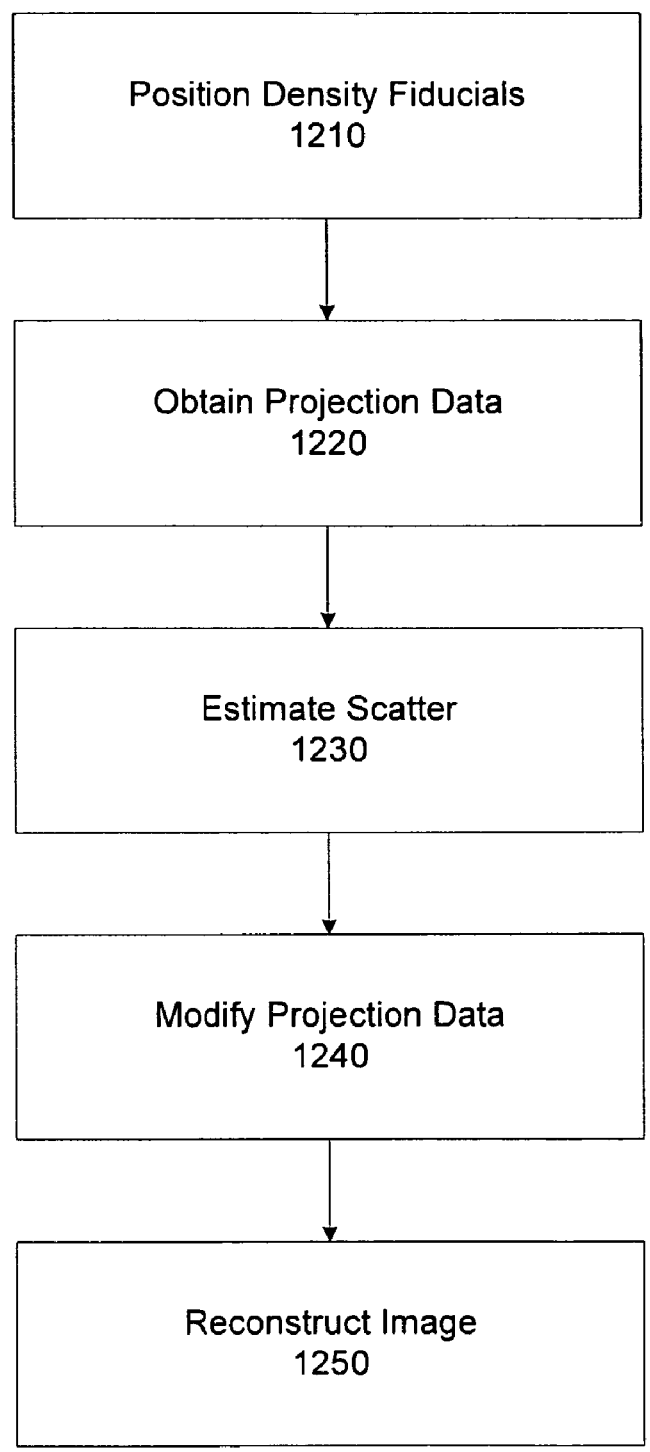
FIG. 12 is a flowchart illustrating a method of using density fiducials to estimate scattered radiation, in accordance with some embodiments of the present invention.

FIG. 12 illustrates a method of obtaining an estimate of radiation scatter by employing density fiducials, in accordance with some embodiments of the present invention. In act 1210, density fiducials may be positioned with respect to an object being imaged. In some embodiments, a proximal density fiducial is positioned between the object and a radiation source adapted to provide radiation to the object. The proximal density fiducial may be partially transmissive to absorb some desired proportion of radiation penetrating the fiducial. In addition, a distal density fiducial may be positioned between the object and a detector array adapted to detect radiation exiting the object. The proximal and distal density fiducials may be selected to have substantially the same density, such that they absorb substantially the same proportion of penetrating radiation.

In act 1220, the object is exposed to radiation to obtain projection data of the object. Multiple exposures may be performed to obtain projection data from a plurality of view angles, distributed uniformly or non-uniformly about the object. In act 1230, the amount of scattered radiation is estimated from the projection data. In particular, the projection data obtained from one or more view angles may be analyzed in connection with the density fiducials to estimate the data. For example, the detector signals from detectors in the shadow of the proximal and distal fiducials from at least one view angle may be compared. As discussed above, discrepancies in the intensity recorded in the shadow of matched pairs of proximal and distal fiducials may be used to indicate the amount of scattered radiation produced by the object.

In act 1240, the projection data is modified to account for the scatter. For example, the contribution to the recorded intensities at the detector array from the estimated scatter may be subtracted from the projection data to remove at least some of the effects of scattered radiation. The modified projection data may then be reconstructed to form an image of the object (act 1250), for example, a 3D image may be obtained from reconstructing the projection data acquired from the plurality of view angles. Therefore, at least some of the image artifacts resulting from scattered radiation may be removed.

In some embodiments, the proximal and distal density fiducials may be affixed directly to the object being imaged. For example, the density fiducials may be an adhesive of a desired density applied directly to the object. In some embodiments, the distal density fiducial is affixed to the detector array. In some embodiments, the object being imaged is a human female breast and a compression mechanism is used to compress the breast and hold the breast in place during the imaging procedure. In such embodiments, the density fiducials may be affixed to and/or be a part of the compression mechanism. As discussed above, the density fiducials may be of any shape, size or density, as the aspects of the invention are not limited in this respect. In some embodiments, the density fiducials are approximately 1 mm$^2$-3 mm$^2$ in area.

In some embodiments, the density fiducials have a density which is in the range between 75% and 150% percent of the density of the predominant density in the object being imaged. In particular, in some imaging procedures, the object being imaged may have a characteristic density and/or may be of a generally homogeneous density, and the density of the fiducials may be selected in view of the characteristic and/or homogeneous density. For example, in mammography, the female human breast is made primarily of fatty tissue, which itself is composed significantly of water. Accordingly, the breast may have a characteristic density of typical breast tissue and the density fiducials may be selected to have some predetermined percentage of that density. In some embodiments, the density fiducials have a density greater than 150% of the characteristic density of the object being imaged. It should be appreciated that density fiducials of any density may be chosen, as the aspects of the invention are not limited in this respect.

As discussed above, partially transmissive density fiducials may be employed to facilitate calibrating the intensity of radiation impinging on the detectors. Reconstructing an image from projection data involves determining the relationship between recorded intensity and the density of the object. Stated differently, image reconstruction may involve mapping recorded intensities to density values. The appropriate mapping may be assisted by placing partially transmissive fiducials of known density within the exposure area. For example, by having subject matter of known density and known location in the exposure area, the recorded intensities at detectors associated with those locations can be assigned the known density values, and other intensity may be mapped accordingly relative to the known mapping at the density fiducials.

It should be appreciated that the intensity to density mapping may not be linear. That is, an increment in recorded intensity may not map to a corresponding increment in density due in part to the exponential attenuation function, beam hardening, scatter etc. Accordingly, the mapping between recorded intensity and density may be some function. The known density values and locations of partially transmissive fiducials, therefore, may be used to determine the slope of the curve that maps recorded intensity values to density values.

In some embodiments, the different intensity reductions caused by proximal and distal density fiducials respectively may be used to estimate beam hardening effects. In particular, if the proximal and distal density fiducials are of the same thickness and are made of the same material, differences in the apparent transmissivity (e.g., as indicated by the recorded intensities) may be due in part to beam hardening. Specifically, because the lower energy radiation is preferentially absorbed, a greater proportion of higher energy radiation will impinge on the distal density fiducial than will impinge on the proximal density fiducial, making the distal density fiducial appear more transmissive. Accordingly, discrepancy between the apparent transmissiveness of the matched density fiducials may be used to approximate the effects of beam hardening.

Figure 13:
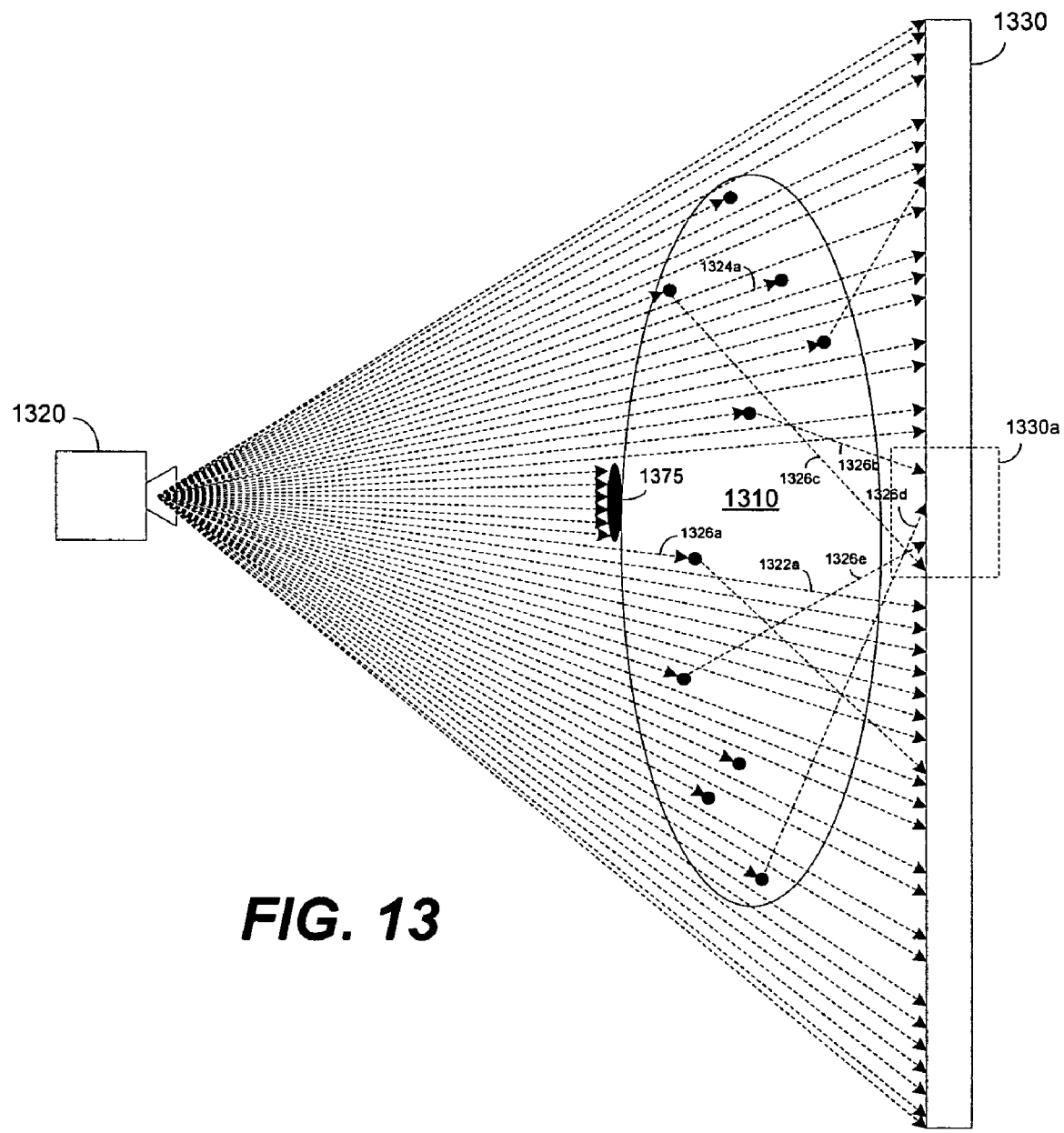
FIG. 13 is a diagram illustrating the use of a substantially opaque density fiducial to estimate scattered radiation.

As an alternative to, or in combination with, partially transmissive density fiducials, one or more density fiducials that are more or less opaque to radiation may be used to gain information that may be used to correct projection data and/or otherwise inform reconstruction about one or more effects not accounted for by the simplified model. FIG. 13 illustrates how an opaque density fiducial may be used to estimate the amount of scattered radiation.

In FIG. 13, a radiation source 1320 is arranged to expose an object 1310 to radiation, and a detector array 1330 is positioned to detect radiation penetrating and exiting the object to collect projection data. Some amount of the radiation emitted by radiation source will be transmitted (e.g., exemplary ray 1322a) to impinge on the detector array, some amount will be absorbed according to the photoelectric effect (e.g., exemplary ray 1324a), and some amount will be scattered according to the Compton effect (e.g., exemplary ray 1326a). However, as discussed above, the transmitted radiation and the scattered radiation impinging on the detector array are generally indistinguishable. As a result, reconstructions that assume detector signals were produced by transmitted radiation alone will suffer from image artifacts associated with incorrectly interpreted detector signals resulting from scattered radiation.

An opaque density fiducial 1375 positioned proximally will absorb radiation impinging on its surface, casting a shadow on the detector array (i.e., on detectors in portion 1330a) wherein no transmitted radiation will impinge. As a result, any radiation detected at portion 1330a can be attributed to scattered radiation. For example, some amount of radiation will be scattered by object 1310 and will impinge within the shadow of the density fiducial (e.g., exemplary scattered rays 1326b-1326e).

The detected radiation may be used to approximate the contribution of scattered radiation on the detector signals. That is, the detector signals generated in region 1330a may be used as a measure of the amount of radiation being scattered by object 1310. The estimate of the scattered radiation may be used to adjust the detector signals to account in part for scatter in the reconstruction of the projection data obtained by exposing object 1310 to radiation from a plurality of view angles. In particular, the detector signal generated by detectors in the shadow of opaque density fiducial 1375 may be used as an estimate of the how much scattered radiation is contributing to the detector signals at detectors that are not in the shadow of the density fiducial. Accordingly, the projection data may be modified to remove contributions estimated as being attributable to scattered radiation. An image reconstructed from the modified projection data, therefore, will have been compensated, to some extent, for scatter effects.

Applicant has identified further methods in which a bootstrap image may be used to inform reconstruction of projection data to reduce and/or eliminate image artifacts, errors or otherwise improve the quality of the resulting image. Applicant has recognized that in conventional reconstruction, due generally to the absence of a priori information about the boundary of the object being imaged, locations outside of the object may be assigned non-zero density values. That is, some of the attenuation contribution will be attributed to surrounding matter such as air. Assigning density values to surrounding matter that contributed negligibly or did not contribute at all to the attenuation of radiation results in assigning incorrect density values to matter within the boundaries of the object.

As will be appreciated by those skilled in the art, image reconstruction from limited projections is generally ill-posed (i.e., there are more unknowns than knowns) such that the reconstruction algorithm operating on given projection data will not have a single unique solution. Accordingly, a reconstruction algorithm, for example, an iterative algorithm such as a gradient descent approach, may converge to a local minimum. Accordingly, the more constraints the algorithm has, the less likely the algorithm will be to converge to a local minimum having relatively significant errors in the distribution of density values.

When intensity is incorrectly assigned outside the boundary of an object, the intensity assigned within the boundary of the object will be incorrectly assigned, approximately to the same extent, resulting in artifacts in the resulting images. Applicant has appreciated that information about the object boundary can be used to constrain the reconstruction to produce an image that is more reflective of the actual density distribution of the object. Artifacts associated with incorrectly assigning intensity values outside the boundary of an object tend to effect the intensity values near the boundary more than intensity levels further away from the boundary. This effect may be particularly deleterious for mammography images where anomalous tissue may be located near the surface of the breast.

In some embodiments, a bootstrap image is reconstructed from projection data obtained by exposing an object to radiation. The bootstrap image is processed to identify a boundary of the object. The identified boundary is used to constrain a second reconstruction of the projection data to form an image representing a density distribution more reflective of the density distribution of the object. In some embodiments, one or more density fiducials are arranged in contact with or proximate to an object to be imaged to define the boundary of the object. A bootstrap image may be reconstructed from projection data obtained during one or more exposures of the object in the presence of the one or more density fiducials. The density fiducials may be identified in the bootstrap image to locate the boundary of the object, and the located boundary used to constrain a second reconstruction of the projection data. Alternatively, recognizable features of the object that are located at the object boundaries can be used to identify the object boundaries. For example, in a breast image, the pattern of the skin may have a detectable property that is recognizable from that of the interior breast tissue.

Figure 14:
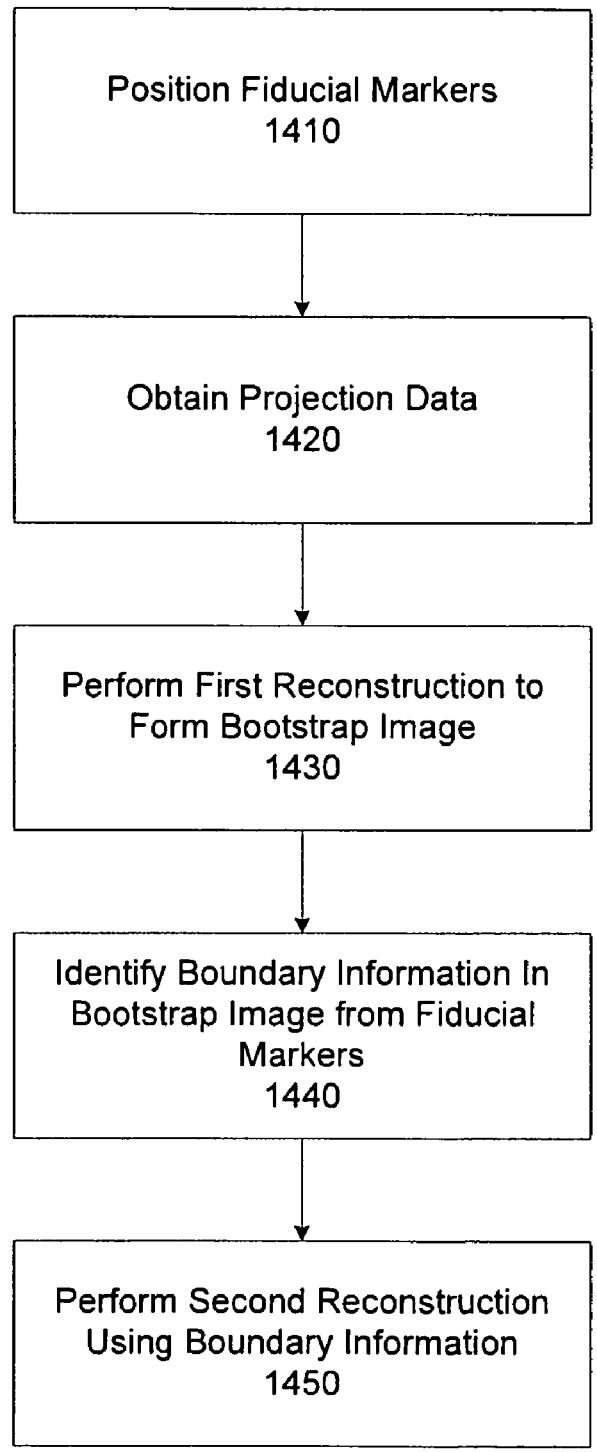
FIG. 14 is a flowchart illustrating a method of using density fiducials to facilitate identifying a boundary of an object being imaged, in accordance with some embodiments of the present invention.

FIG. 14 illustrates a method of using boundary information to constrain a reconstruction of projection data, in accordance with various embodiments of the present invention. In act 1410, one or more density fiducials are positioned in contact or proximate the boundary of an object to be exposed to radiation. Preferably, one or more of the density fiducials are placed in contact with the object to demarcate the boundary. The one or more density fiducials may be made of a material having a density that is salient with respect to the object such that it is relatively easy to identify in an image. For example, the one or more density fiducials may be partially transmissive or partially opaque to radiation emitted by a radiation source during an exposure. As a result, the one or more density fiducials may be relatively easy to locate in a reconstructed image, for example, using any of various automatic image processing algorithms.

In some embodiments, a plurality of density fiducials are spaced apart as to not block substantial amounts of radiation. The plurality of spaced apart density fiducials may be used to identify portions of the boundary of the object. The boundary of the object between the density fiducials may be interpolated and/or otherwise determined based on general knowledge about the shape of the object. For example, in breast imaging, the breast shape is generally known (e.g., the breast, when compressed, is generally elliptical and has a generally continuous and smoothly transitioning boundary) and gaps in the boundary between density fiducials may be approximated, interpolated or otherwise determined based on this knowledge. For example, one or more curves may be fit between the density fiducials to approximate the boundary.

In addition, other image processing techniques may be used to determine the boundary between the density fiducials such as edge detection and/or the detection of other morphological characteristics of the boundary of the object, as discussed in further detail below. It should be appreciated that density fiducials (when opaque) prevent radiation from being transmitted through the breast underneath the shadow of the density fiducial. Accordingly, it may be beneficial to place the density fiducials strategically. For example, in breast imaging, it may be beneficial to place the density fiducials at boundary locations of higher curvature where it may be more difficult to interpolate between density fiducials.

While opaque density fiducials block radiation that may otherwise carry information about the structure of the object, it should be appreciated that in imaging procedures where projection data is obtained from a plurality of view angles, the density fiducials will cast a shadow on different portions of the object at each view angle. Accordingly, the different views may be used to ensure that sufficient information about all parts of the object are captured in the projection data. Alternatively, partially transmissive density fiducials may be used that facilitate detecting the object boundary, but permit a desired proportion of radiation to penetrate the object.

In one embodiment, the one or more density fiducials are a flexible material that conforms to the shape of the object being imaged. The flexible material may have a known outer boundary that can be identified. The one or more density fiducials may also be part of the imaging apparatus designed to hold the object in place. For example, in breast imaging, a compression mechanism may be positioned to hold and compress the breast in place. One or more density fiducials adapted to facilitate identifying the boundary of the object may be affixed to or be part of the compression mechanism. It should be appreciated that any type of density fiducial that facilitates identifying the boundary of the object may be used, as the aspects of the invention are not limited in this respect.

In act 1420, projection data is obtained of an object by exposing the object to radiation from one or more view angles. For example, the projection data may be obtained from a number of view angles distributed uniformly or non-uniformly about the object. However, the projection data may result from a single view angle, as the aspects of the invention are not limited in this respect. In act 1430, a first reconstruction is performed on the projection data to form a bootstrap image of the object. The bootstrap image may be a 2D image, a plurality of 2D images and/or a 3D image of the object. Since the projection data was obtained in the presence of the one or more density fiducials, evidence of the density fiducials will be present in the bootstrap image (i.e., the one or more density fiducials will be imaged).

In act 1440, the image of the one or more density fiducials are located in the bootstrap image to obtain boundary information indicative of the boundary of the object. For example, the bootstrap imaged may be processed and areas of relatively high density characteristic of the density fiducials may be identified. The areas of high density are then considered to include locations along the boundary of the object. This boundary information may then be used to constrain a second reconstruction to avoid errors resulting from incorrectly assigning density values to locations outside the boundary of the object being imaged.

In addition to the boundary information derived directly from the density fiducials, the boundary may be further defined using other methods. For example, the boundary of the object between density fiducials may be approximated using interpolation, by fitting one or more curves between the density fiducials and/or by using known information about the general shape of the object being imaged. In addition, various other image processing techniques may be used to detect more of the object boundary to improve the boundary information used in the second reconstruction.

For example, edge detection may be used to locate the boundary of the object. One or more segmentation algorithms may be used to segment the object to define its boundary. For example, the one or more density fiducials could be used as a basis for seeding a region growing algorithm configured to segment the object from non-object material, the border between the segmented regions operating as the boundary of the object. In addition, one or more morphological characteristics may be used to locate the boundary. For example, the boundary of a given object may have characteristics that result in detectable image properties that can be identified during processing of the bootstrap image. For example, in breast imaging, the skin typically results in a characteristic pattern that can be identified by the appropriate image processing algorithm.

In some embodiments, the boundary may be identified without the aid of density fiducials. For example, act 1410 may not be performed in some embodiments. Instead, the boundary may be identified using morphological characteristics and/or any other detectable properties of the object in the image to identify the boundary. For example, in breast imaging, the characteristic pattern of the skin may be used to identify the boundary. However, any of various image processing techniques, pattern recognition and/or computer vision techniques may be used to identify and locate the boundary, as the aspects of the invention are not limited in this respect.

In addition, the boundary of an object may be identified manually. For example, an operator may indicate the location of density fiducials, the location of the boundary, or a combination of both. Manual techniques may be performed in combination with automatic techniques to obtain boundary information about the object from the bootstrap image. In some embodiments, instead of identifying boundary information in the bootstrap image, boundary information is identified in the projection data (e.g., in each of the 2D projections). A 3D reconstruction algorithm can then be employed to form a 3D boundary map of from the boundaries identified in each of the projections. This 3D map can then be used to constrain a reconstruction of a 3D image. Any one or combination of techniques may be employed to obtain boundary information from the bootstrap image or the 2D projections, as the aspects of the invention are not limited in this respect.

In act 1450, the boundary information obtained in act 1440 is used to constrain a second reconstruction of the projection data. As discussed above, the lack of knowledge about the boundary of the object may lead to density values being incorrectly assigned outside the object, which in turn may prevent the density values from being correctly distributed inside the object. Accordingly, the boundary information may be used to instruct the reconstruction as to where the boundary of the object lies so that density values are not assigned to locations outside the object.

In some embodiments, a zero density value is assigned to each location outside the object to initialize the reconstruction. The constraints imposed by the boundary information may facilitate a reconstruction that is better posed, reducing the likelihood of the reconstruction algorithm converging to an undesirable local minimum or otherwise resulting in a solution that does not accurately reflect the density distribution of the object (e.g., local minimums where density values are assigned outside the boundary of the object). It should be appreciated that the boundary information may be used in any way to improve the reconstruction of the projection data, as the aspects of the invention are not limited in this respect.

Certain imaging procedures, and more particularly, various medical imaging procedures may have substantial imaging times. For example, an imaging interval may include obtaining projection data from a plurality of view angles, in between which components of the imaging apparatus may need to be moved to new locations associated with the corresponding view angle (e.g., a radiation source and/or detector array may need to be rotated about the object being imaged). During the imaging interval, the object being imaged should remain relatively motionless to prevent motion blur. For example, in medical imaging procedures, motion by a human subject during exposure from different view angles may result in projection data that is misaligned.

Images reconstructed from the misaligned data may appear blurry, or washed out, and may be unsuitable for diagnostic purposes. The ability to detect subject motion may be important to timely alert an operator that the imaging procedure may need to be repeated. For example, it may advantageous to alert an operator that the imaging procedure may need to be repeated before the patient leaves the medical imaging facility, and preferably while the patient is still positioned in the imaging apparatus.

The operator of a piece of imaging equipment (e.g., a technician) tasked with obtaining one or more images of a subject, may not be a radiologist and/or may not be trained in analyzing medical images. Accordingly, by the time a radiologist can view the images and determine that the imaging procedure needs to be repeated, the subject may have left the imaging apparatus and/or left the facility. Applicant has developed methods of automatically detecting subject motion to timely alert an operator without the images having to be inspected. By automatically detecting subject motion, an imaging procedure may be repeated immediately (e.g., before the subject is removed from the imaging apparatus). In some embodiments, projection data obtained from multiple exposures at the same view angle may be compared to determine whether a subject has moved in the time between the exposures.

Figure 15:
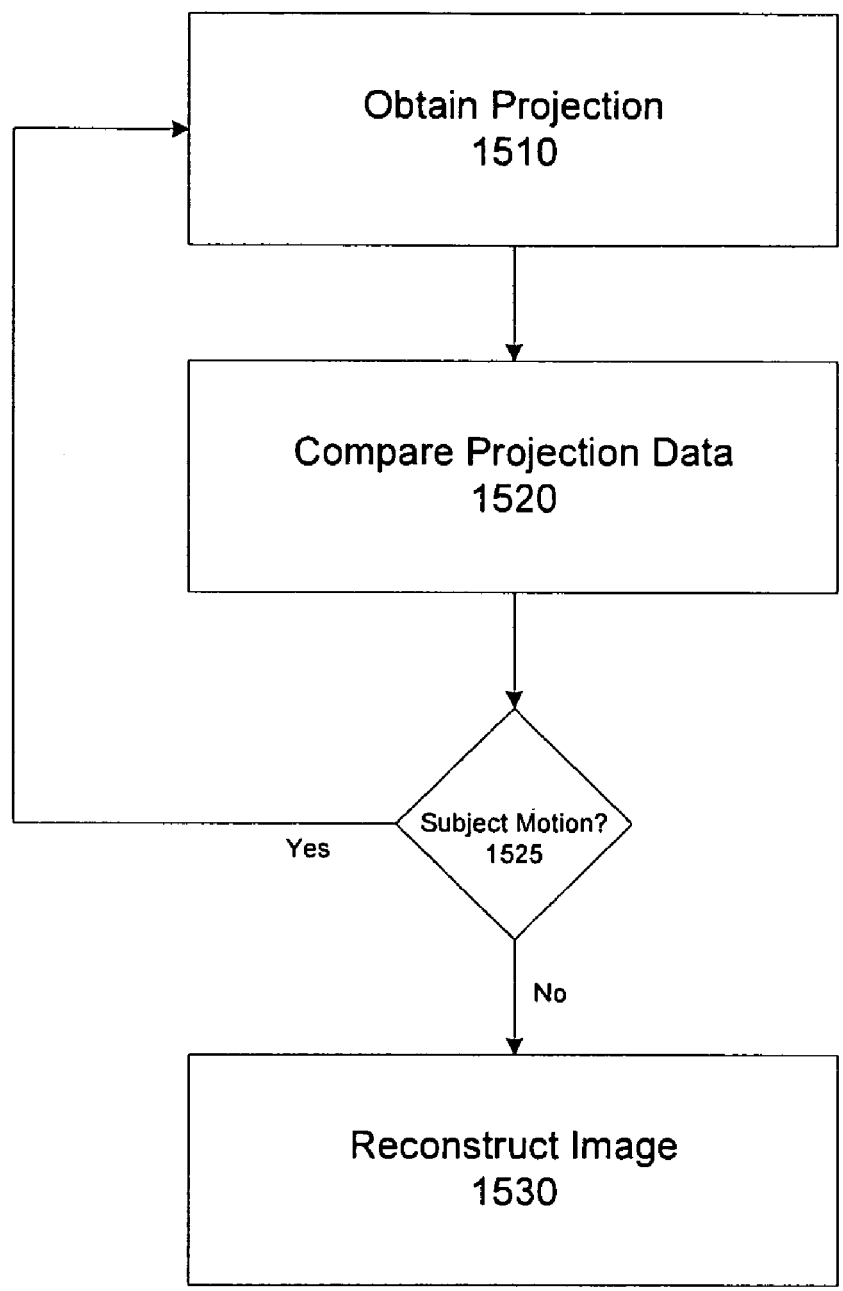
FIG. 15 is a flowchart illustrating a method of detecting subject motion, in accordance with some embodiments of the present invention.

FIG. 15 illustrates a method of automatically detecting subject motion, in accordance with some embodiments of the present invention. In act 1510, projection data is obtained of a subject from a plurality of view angles. For example, projection data may be obtained according to any of the methods described above, or as described in the '848 patent. As part of obtaining the projection data in act 1510, projection data is obtained from multiple exposures from the same view angle. Exposures from at least one other view angle may be obtained in between the multiple exposures from the same angle such that some finite amount of time passes between the exposures at the same view angle.

For example, projection data may be obtained initially from a first view angle. As the imaging procedure continues, projection data may be obtained from a plurality of different view angles according to any desired exposure plan. For example, projection data may be obtained from a plurality of view angles that are distributed uniformly or non-uniformly about a portion of the subject being imaged. After exposures at each of the plurality of view angles have been performed, a second exposure may be performed at the first view angle to obtain additional projection data.

The second exposure at the first view angle need not be performed after all other exposures have been performed, and more than one repeat exposure may be performed at the first view angle. In addition, the repeat exposures need not be performed at the first view angle, as the aspects of the invention are not limited in this respect. It may be preferable, however, to take exposures from the same view angle at the beginning and end of the imaging procedure so that the projection data from the repeat exposures are likely to capture subject motion throughout. A repeat exposure may be obtained in the middle of the procedure (or at any time) to capture information about subject motion at any desired moment during the imaging procedure.

In act 1520, the projection data obtained from the multiple exposures at the same view angle are compared to determine if the subject moved between exposures. For example, if the subject has not moved or has moved negligibly, the projection data at each of the multiple exposures from the same view angle should be substantially the same. However, if the subject has moved by any appreciable amount, the projection data will be different for exposures from the same view angle between which the subject moved. In some embodiments, projection data from different exposures at the same view angle are subtracted from one another. The magnitude of the difference may be indicative of the extent of the subject motion. In some embodiments, a correlation is made between projection data obtained from each of the multiple exposures. High degrees of correlation will indicate that the subject did not move appreciably. Likewise, uncorrelated data may indicate subject motion. The projection data from multiple exposures at the same view angle may be compared in other ways to determine the presence of, or the extent of subject motion, as the aspects of the invention are not limited in this respect.

In act 1525, it may be determined if there was significant enough subject motion to merit repeating the imaging procedure. For example, if the magnitude of the difference between projection data obtained from multiple exposures is above a predetermine threshold, or the projection data is too uncorrelated, an alert may be generated to instruct an operator to perform the imaging procedure again. If the comparison of the projection data indicates that there was no or substantially no subject motion, the projection data may be reconstructed to form one or more images of the portion of the subject (act 1530). For example, the imaging procedure may be part of a breast examine, and the projection data may be reconstructed to form an image of the breast to be analyzed by a radiologist. By automatically detecting subject motion, the breast imaging may be repeated, if need be, before the patient is removed from the imaging apparatus and/or leaves the imaging facility.

In some embodiments, motion detection may be achieved without having to obtain multiple exposures at the same view angle. For example, projection data obtained from a plurality of view angles may be reconstructed to form a 3D image. Computed projection data may be obtained by computationally projecting the 3D image onto a plurality of 2D planes (e.g., deconstructing the 3D image is a process related to the inverse of image reconstruction). Computing projection data simulates computationally the process projecting the object onto the detectors by exposing the object to radiation. The computed projection data may then be compared to the observed projection data obtained from exposing the object from the plurality of view angles. Differences in the computed and observed projection data may be indicative of motion of the subject. For example, a shift in the position of a high-contrast feature between the calculated and observed projection data could be used to identify object motion. Alternatively, mathematical operators such as the convolution or cross-correlation operators could be used to identify objection motion.

In another variant of this method, one or more of the observed projections of the object obtained by exposing the object to radiation at a corresponding view angle may be excluded from the initial 3D reconstruction. Computed projection data may then be generated that corresponds to each of the excluded projections (i.e., computed projection data may be computed for the view angles from which the observed projections were excluded). A comparison of the computed projection data with the excluded observed projections may be used to identify object motion using the methods described above.

Figure 16:
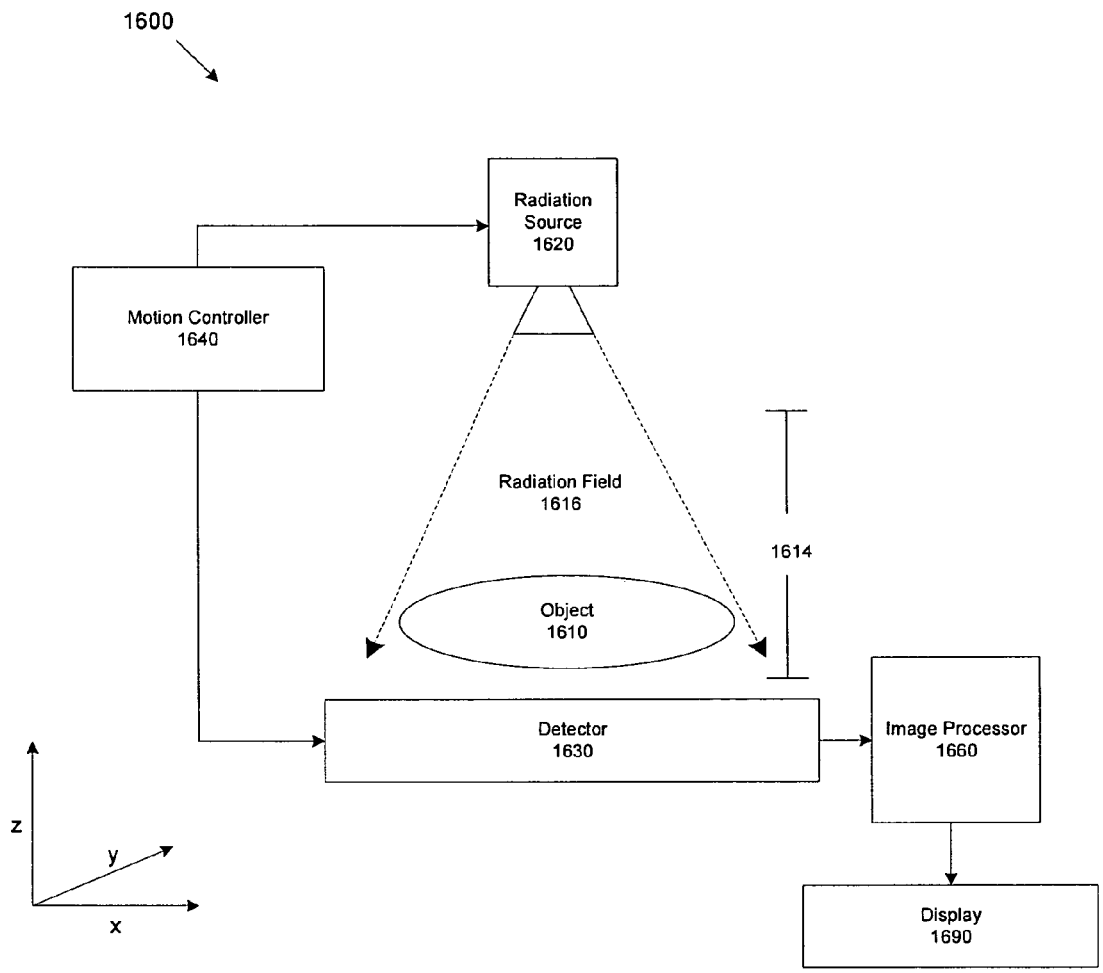
FIG. 16 is a diagram of an imaging apparatus suitable for implementing various aspects of the present invention.

FIG. 16 illustrates an imaging apparatus that may be used to perform various methods described above, in accordance with some embodiments of the present invention. Imaging system 1600 may be suitable, for example, for obtaining projection data to be reconstructed to form 3D images in a relatively low-dose environment, in accordance with various aspects of the present invention. Imaging system 1600 may be suitable for obtaining projection data and reconstructing images according to the various methods described in the '848 patent, the '664 application, and/or for performing any one or combination of methods described in the foregoing.

Imaging system 1600 includes a radiation source 1620, a detector 1630, a motion controller 1640, an image processor 1660 and a display 1690. The imaging system 1600 can be used to image a single object 1610 or a plurality of objects located within an exposure area 1614. The exposure area 1614 defines generally the region of space between the radiation source 1620 and the detector 1630, and is located in the path of the radiation provided by radiation source 1620 in the direction of detector 1630. The exposure area 1614 may be the entire region of space located in the path of the radiation passing from the radiation source 1620 to the detector 130, or only a predetermined portion of the space.

Radiation source 1620 may be any component or combination of components capable of emitting radiation such as x-ray or gamma radiation. In imaging system 1600, radiation source 1620 is positioned to emit radiation toward exposure area 1614 such that, when object 1610 is present in exposure area 1614, at least some of the radiation impinges on object 1610. In particular, the radiation source 1620 is adapted to emit radiation to form a radiation field 1616, which may be of any shape or size. In a preferred embodiment, radiation field 1616 is a beam that radiates outward from a focal point of radiation source 1620 substantially in the shape of a cone, and that substantially encloses object 1610 within a cone of x-rays during exposures. However, radiation field 1616 may form other shapes such as a fan beam, pencil beam, etc., and may be arranged to expose any portion of object 1610, as the aspects of the invention are not limited in this respect.

Radiation source 1620 is capable of being moved about object 1610 such that radiation may be directed at object 1610 from a plurality of angular positions, i.e., a plurality of view angles with respect to object 1610 (e.g., as described in further detail below). Detector 1630 is positioned to receive at least some of the radiation that passes through the exposure area 1614, and in particular, radiation that has penetrated and exited object 1610. Detector 1630 may be a single detector, or a detector array disposed continuously or at a plurality of discrete locations. Detector 1630 may be formed from any type of material responsive to radiation generated by radiation source 1620. In response to impinging radiation, detector 1630 produces signals indicative of the intensity of radiation impinging on the detector surface. Accordingly, recorded intensities of radiation passing through the object as represented by the detector signals carry information about the absorption characteristics of object 1610, and form, at least in part, projection data of object 1610.

Detector 1630 may be configured to be moved in correspondence with the radiation source 1620 to detect radiation exiting object 1610 from the plurality of view angles. Motion controller 1640 may be coupled to radiation source 1620 and detector 1630 to cause the rotational movement of the radiation source/detector apparatus such that, as the apparatus rotates about the object, the object remains positioned within the exposure area between the source and detector. Motion controller 1640 may be capable of being programmed to move the radiation source and detector to any desired view angle with respect to object 1610. Together, the radiation source 1620, detector 1630 and motion controller 1640 permit projection data of object 1610 to be obtained from any set of view angles. In some embodiments, motion controller 1640 may be programmed to control the position of the radiation source and detector independently. For example, the motion controller may move the radiation source and detector along different paths as projection data is obtained from the different view angles, as the aspects of the invention are not limited in this respect.

In another embodiment, the detector 1630 remains stationary as the radiation source is moved about the object. For example, if the detector 1630 is sufficiently large (e.g., a flat panel two-dimensional detector array) and/or if the angular range over which projection data is obtained is sufficiently small (e.g., the angular range is limited to a range between 5° and 45° both clockwise and counterclockwise from a reference view angle), a single position for the detector 1630 may be sufficient to capture projection data from each of the desired view angles. In addition, in embodiments where detector 1630 remains stationary, the object may be positioned in direct contact with the detector.

At each view angle, the detector signal generated by each detector in the array indicates the total absorption (i.e., attenuation) incurred by material substantially in a line between the radiation source and the detector. Therefore, the array of detection signals at each view angle records the projection of the object onto the detector array at the associated view angle. For example, using a 2D detector array, the resulting detector signals represent the 2D density projection of the object on the detector array at the corresponding view angle. The signals generated by the detectors form, at least in part, projection data (or view data) of the object.

Image processor 1660 may be configured to reconstruct the projection data to form images of the object (e.g., 2D or 3D images of the object). Image processor 1660 may be configured to implement any desired reconstruction algorithm capable of mapping recorded radiation intensity values (e.g., detector signals from detector 1630) to corresponding density values. Image processor 1660 may also be configured to automatically process reconstructed images to obtain data from the images to, for example, modify the projection data and/or inform a subsequent reconstruction of the projection data.

Image processor may be one or more processors located proximate or remote from the radiation source and detector. The image processor may be configured to execute programs stored on a computer readable medium such as a memory accessible by the image processor. Imaging system 1600 may also include a display 1690, such as a monitor, screen and/or other display device capable of presenting a pixel representation of reconstructed image data. It should be appreciated that the above described components are merely exemplary, and any suitable imaging apparatus of any configuration and/or combination of components may be used to implement any one or combination of the methods described above, as the aspects of the invention are not limited in this respect.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed function. The one or more controller can be implemented in numerous ways, such as with dedicated hardware, or with general purpose hardware (e.g., one or more processor) that is programmed using microcode or software to perform the functions recited above.

It should be appreciated that the various methods outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code.

In this respect, it should be appreciated that one embodiment of the invention is directed to a computer readable medium (or multiple computer readable media) (e.g., a computer memory, one or more floppy discs, compact discs, optical discs, magnetic tapes, etc.) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

It should be understood that the term "program" is used herein in a generic sense to refer to any type of computer code or set of instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. The invention is capable of other embodiments and of being practiced or of being carried out in various ways. In particular, various aspects of the present invention may be implemented in connection with any type, collection or configuration networks. No limitations are placed on the network implementation. Accordingly, the foregoing description and drawings are by way of example only.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. A method of imaging an object of interest positioned in an exposure area, the method comprising:
    obtaining projection data of the object by providing radiation from a radiation source to the exposure area and detecting, by at least one detector, at least some of the radiation exiting the object to form the projection data;
    performing a first reconstruction of the projection data to form at least one bootstrap image;
    obtaining first data based on information provided by the at least one bootstrap image including estimating an exit spectrum indicative of the energy spectrum of radiation exiting the object based, at least in part, on density information provided by the at least one bootstrap image; and
    performing a second reconstruction of the projection data based, at least in part, on the first data to form at least one second image.

2. The method of claim 1, wherein estimating the exit spectrum includes estimating an emission spectrum indicative of the energy spectrum of radiation emitted by the radiation source.

3. The method of claim 2, wherein estimating the exit spectrum includes modifying the emission spectrum based on the density information in the at least one bootstrap image to estimate the exit spectrum.

4. The method of claim 1, wherein performing the second reconstruction includes performing the second reconstruction using the exit spectrum to account for at least some beam hardening effects.

5. The method of claim 1, wherein the first reconstruction is performed assuming that the detected radiation is substantially of a single energy, and the second reconstruction is performed assuming that the detected radiation includes energies distributed according to the exit spectrum.

6. The method of claim 5, wherein further comprising differentiating portions of the detected radiation contributive by respective energies in the exit spectrum.

7. The method of claim 6, further comprising, computing, from the detected radiation and based on the exit spectrum, a radiation intensity of radiation at a plurality of energies present in the exit spectrum.

8. The method of claim 7, wherein the second reconstruction is performed by reconstructing the radiation intensity for each of the plurality of energies according to a respective attenuation function characteristic of the respective energy.

9. The method of claim 1, wherein obtaining the first data includes obtaining information about locations of material within the object to facilitate estimating an amount of scattered radiation.

10. The method of claim 1, wherein obtaining first data includes obtaining boundary information indicative of a boundary of the object in the at least one bootstrap image.

11. The method of claim 10, wherein performing the second reconstruction includes using the boundary information to constrain the second reconstruction.

12. A method of imaging an object of interest positioned in an exposure area, the method comprising:
obtaining projection data of the object by providing radiation from a radiation source to the exposure area and detecting, by at least one detector, at least some of the radiation exiting the object to form the projection data;
performing a first reconstruction of the projection data to form at least one bootstrap image;
obtaining first data based on information provided by the at least one bootstrap image including obtaining information about locations of material within the object to facilitate estimating an amount of scattered radiation;
performing a second reconstruction of the projection data based, at least in part, on the first data to form at least one second image;
dividing an image of the object in the at least one bootstrap image into a plurality of regions;
determining a depth of each of the plurality of regions with respect to a reference point related to a radiation source that provides the radiation to the exposure area;
estimating an amount of scattered radiation resulting from each of the plurality of regions based on the possibility that radiation passing through the respective region would scatter at the associated depth;
summing the estimates of scattered radiation to provide an estimate of the total scattered radiation; and
modifying the projection data based, at least in part, on the estimate of the total scattered radiation.

13. A method of imaging an object of interest positioned in an exposure area, the method comprising:
obtaining projection data of the object by providing radiation from a radiation source to the exposure area and detecting, by at least one detectors, at least some of the radiation exiting the object to form the protection data;
performing a first reconstruction of the projection data to form at least one bootstrap image;
obtaining first data based on information provided by the at least one bootstrap image including obtaining boundary information indicative of a boundary of the object in the at least one bootstrap image, wherein obtaining the boundary information includes determining which pixels in the bootstrap image are outside of the boundary of the object, and wherein constraining the second reconstruction includes assigning zero-density values to pixels identified as being outside the boundary of the object; and
performing a second reconstruction of the projection data based, at least in part, on the first data to form at least one second image including using the boundary information to constrain the second reconstruction.

14. A method of imaging an object of interest positioned in an exposure area, the method comprising:
obtaining projection data of the object by providing radiation from a radiation source to the exposure area and detecting, by at least one detector, at least some of the radiation exiting the object to form the projection data;
arranging at least one density fiducial in the exposure area, prior to obtaining the projection data, such that at least some of the radiation encounters the at least one density fiducial;
performing a first reconstruction of the projection data to form at least one bootstrap image;
obtaining first data based on information provided by the at least one bootstrap image; and
performing a second reconstruction of the projection data based, at least in part, on the first data to form at least one second image.

15. The method of claim 14, wherein arranging the at least one density fiducial includes arranging at least one density fiducial in contact with the object to demarcate at least a portion of a boundary of the object.

16. The method of claim 15, wherein obtaining the first data includes obtaining boundary information indicative of a boundary of the object based at least in part on the image of the at least one density fiducial in the bootstrap image.

17. The method of claim 16, wherein reconstruction includes constraining the second reconstruction based on the boundary information.

18. The method of claim 17, wherein constraining the second reconstruction includes assigning zero-density values to regions indicated, by the boundary information, as being outside the boundary of the object.

* * * * *